(12) United States Patent
Xu et al.

(10) Patent No.: US 7,186,551 B1
(45) Date of Patent: Mar. 6, 2007

(54) 3'-PHOSPHOADENOSINE - 5'-PHOSPHOSULFATE SYNTHETASE 2 (PAPSS2) SEQUENCE VARIANTS

(75) Inventors: Zhenhua Xu, Bridgewater, NJ (US); Eric D. Wieben, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 486 days.

(21) Appl. No.: 10/294,397

(22) Filed: Nov. 14, 2002

Related U.S. Application Data

(60) Provisional application No. 60/332,685, filed on Nov. 14, 2001.

(51) Int. Cl.
C12N 15/11 (2006.01)
C12N 15/54 (2006.01)
C12N 15/63 (2006.01)
C12N 9/10 (2006.01)
C12N 9/12 (2006.01)

(52) U.S. Cl. .............. 435/320.1; 536/23.2; 536/24.3; 536/24.31; 536/23.1; 435/193; 435/194

(58) Field of Classification Search ............ 536/23.2, 536/24.3, 24.31; 435/193, 194, 320.1
See application file for complete search history.

(56) References Cited

U.S. PATENT DOCUMENTS

| | | | |
|---|---|---|---|
| 5,451,683 | A | 9/1995 | Barrett et al. |
| 5,733,729 | A | 3/1998 | Lipshutz et al. |
| 5,770,722 | A | 6/1998 | Lockhart et al. |
| 2001/0053519 | A1* | 12/2001 | Fodor et al. ............... 435/6 |

FOREIGN PATENT DOCUMENTS

| WO | WO 98/20019 | 5/1998 |
|---|---|---|
| WO | WO 99/57318 | 11/1999 |

OTHER PUBLICATIONS

K.Kurima et al. "A Member of a Family of Sulfate-Activiating Enzymes Causes Murine Brachymorphophism". PNAS 95: 8681-8685. (Jul. 1998).*
Z. Xu et al. "Hu7man 3'Phosphoadenosine 5'Phosphosulfate Synthetase 2 (PAPSS2) Pharmacogenetics: Gene resequencing, Genetic polymorphisms and Functional Characterization of Variant Allozymes", Pharmacogenetics 12:11-21. (Jan. 2002).*
T. Ikeda et al. "Identification of Sequence Polymorphisms in Two Sulfation-Related Genes, PAPSS2 and SLC26A2, and an Association Analysis With Knee Osteoarthritis", J.Human Genetics 46: 538-543. (Sep. 2001).*
GenBank Accession No. BG990709 (Jun. 2001).*
GenBank Accession No. AW180412. (Nov. 1999).*

Aksoy et al., "Human Liver Estrogen Sulfotransferase: Identification By cDNA Cloning and Expression", *Biochem. Biophys. Res. Commun.*, 1994, 200:1621-1629.

Chadwick et al., "Heterozygote and Mutation Detection by Direct Automated Fluorescent DNA Sequencing Using a Mutant Taq DNA Polymerase", *Biotechniques*, 1996, 20:676-683.

Cibelli et al., "Cloned Transgenic Calves Produced from Nonquiescent Fetal Fibroblasts", *Science*, 1998, 280:1256-1258.

Cleland, "Computer Programmes for Processing Enzyme Kinetic Data", *Nature*, 1963, 198:463-465.

Cole et al., "The EBV-Hybridoma Technique and its Application to Human Lung Cancer", *Monoclonal Antibodies and Cancer Therapy*, 1985, Alan R. Liss, Inc. pp. 77-96.

Collins et al., "A DNA Polymorphism Discovery Resource for Research on Human Genetic Variation", *Genome Res.*, 1998, 8:1229-1231.

Cote et al., "Generation of human monoclonal antibodies reactive with cellular antigens", *Proc. Natl. Acad. Sci. USA*, 1983, 80:2026.

Flohe et al., "Kinetics of Purified Catechol O-Methyltransferase", *Biochim. Biophys. Acta*, 1970, 220:469-476.

Gordon et al., "*Consed*: A Graphical Tool for Sequence Finishing", *Genome Res.*, 1998, 8:195-202.

Guatelli et al., "Isothermal, *in vitro* amplification of nucleic acids by a multienzyme reaction modeled after retroviral replication", *Proc. Natl. Acad. Sci. USA*, 1990, 87:1874-1878.

Hacia et al., "Detection of heterozygous mutations in *BRCA1* using high density oligonucleotide arrays and two-colour fluorescence analysis", *Nature Genet.*, 1996, 14:441-447.

Hartl and Clark, "Chromosomes and Heredity", *Principles of Populations Genetics*, 3$^{rd}$ Edition, 1997, Sinauer Associates, Inc., Sunderland, MA, pp. 96-107.

Hedrick, "An Introduction to Gametic Disequilibrium", *Genetics of Populations*, 2$^{nd}$ Edition, 2000, Jones and Barlett, Sudbury, MA, pp. 396-405.

Ho et al., "Site-directed mutagenesis by overlap extension using the polymerase chain reaction", *Gene*, 1989, 77(1):51-59.

Huse et al., "Generation of a Large Combinatorial Library of the Immunoglobulin Repertoire in Phage Lambda", *Science*, 1989, 246:1275-1281.

Hyrup et al., "Peptide Nucleic Acids (PNA): Synthesis, Properties and Potential Applications", *Bioorgan. Med. Chem.*, 1996, 4(1):5-23.

Kohler et al., "Continuous cultures of fused cells secreting antibody of predefined specificity", *Nature*, 1975, 256:495-497.

Kozbor et al., "The production of monoclonal antibodies from human lymphocytes", *Immunology Today*, 1983, 4:72-79.

(Continued)

*Primary Examiner*—Rebecca Prouty
(74) *Attorney, Agent, or Firm*—Fish & Richardson P.C.

(57) ABSTRACT

Isolated PAPSS2 nucleic acid molecules that include a nucleotide sequence variant and nucleotides flanking the sequence variant are described, as well as PAPSS2 allozymes. Methods for determining if a mammal is predisposed to joint disease or cancer also are described.

18 Claims, 7 Drawing Sheets

OTHER PUBLICATIONS

Lewis, "PCR's Competitors Are Alive and Well and Moving Rapidly Towards Commercialization", *Genetic Engineering News*, 1992, 12(9):1.

Myakishev et al., "High-Throughput SNP Genotyping by Allele-Specific PCR with Universal Energy-Transfer-Labeled Primers", *Genome*, 2001, 11(1):163-169.

Nickerson et al., "PolyPhred: automating the detection and genotyping of single nucleotide substitutions using fluorescence-based resequencing", *Nucl. Acids Res.*, 1997, 25:2745-2751.

Prince et al., "Robust and Accurate Single Nucleotide Polymorphism Genotyping by Dynamic Allele-Specific Hybridization (DASH): Design Criteria and Assay Validation", *Genome Res.*, 2001, 11(1):152-162.

Quandt et al., "MatInd and MatInspector: new fast and versatile tools for detection of consensus matches in nucleotide sequence data", *Nucl. Acids Res.*, 1995, 23:4878-4884.

Schafer et al., "DNA variation and the future of human genetics", *Nat. Biotechnol.*, 1995, 15:33-39.

Shastry, "Gene disruption in mice: Models of development and disease", *Mol. Cell Biochem.*, 1998, 181(1-2):163-179.

Stephens et al., "Haplotype Variation and Linkage Disequilibrium in 313 Human Genes", *Science*, 2001, 293:489-493.

Stoneking et al., "Population Variation of Human mtDNA Control Region Sequences Detected by Enzymatic Amplification and Sequence-specific Oligonucleotide Probes", *Am. J. Hum. Genet.*, 1991, 48:370-382.

Summerton and Weller, "Morpholino Antisense Oligomers: Design, Preparation, and Properties", *Antisense Nucleic Acid Drug Dev.*, 1997, 7(3):187-195.

Terwilliger and ott, "Linkage Disequilibrium between Alleles at Marker Loci", *Handbook of Human Genetic Linkage*, 1994, The Johns Hopkins University Press, Baltimore, pp. 188-193.

Tilgmann et al., "Purification and partial characterization of rat liver soluble catechol-*O*-methyltransferase". *FEBS*, 1990, 264:95-99.

Underhill et al., "Detection of Numerous Y Chromosome Biallelic Polymorphisms by Denaturing High-Performance Liquid Chromatography", *Genome Res.*, 1997, 7:996-1005.

Venkatachalam et al., "Molecular Cloning, Expression, and Characterization of Human Bifunctional 3'-Phosphoadenosine 5'-Phosphosulfate Synthase and Its Functional Domains", *J. Biol. Chem.*, 1998, 273:19311-19320.

Wakayama et al., "Full-term development of mice from enucleated oocytes injected with cumulus cell nuclei", *Nature*, 1998, 394(6691):369-374.

Weiss, "Hot Prospect for New Gene Amplifier", *Science*, 1991, 254:1292-1293.

Wilkinson, Statistical Estimations in Enzyme Kinetics, *Biochem. J.*, 1961, 80:324-332.

Wilmut et al., "Viable offspring derived from fetal and adult mammalian cells", *Nature*, 1997, 385(6619):810-813.

Wong et al., "Human GM-CSF: Molecular Cloning of the Complementary DNA and Purification of the Natural and Recombinant Proteins", *Science*, 1985, 228:810-815.

Wood et al., "Human Liver Thermolabile Phenol Sulfotransferase: cDNA Cloning, Expression and Characterization", *Biochem. Biophys. Res. Commun.*, 1994, 198:1119-1127.

Xu et al., "Human 3'-Phosphoadenosine 5'-Phosphosulfate Synthetase: Radiochemical enzymatic Assay, Biochemical Properties, and Hepatic Variation", *Biochem. Biophys. Res. Commun.*, 2000, 268(2):437-444.

Xu et al., "Human 3'-Phosphoadenosine 5'-Phosphosulfate Synthetase 1 (PAPSS1) and PAPSS2: Gene Cloning, Characterization and Chromosomal Localization", *Drug. Metab. Dispos.*, 2001, 29(2):172-178.

GenBank Accession No. AF091242, (Oct. 1998).
GenBank Accession No. AF160503, (Mar. 2000).
GenBank Accession No. AF160504, (Mar. 2000).
GenBank Accession No. AF160505, (Mar. 2000).
GenBank Accession No. AF160506, (Mar. 2000).
GenBank Accession No. AF160507, (Mar. 2000).
GenBank Accession No. AF160508, (Mar. 2000).
GenBank Accession No. AF160509, (Mar. 2000).

* cited by examiner

FIGURE 1 – page 1

```
tggaagcccctcagcacgatgcatagtgaacagacaagctgtgaaccttgggagttatca
ccatgtgtgatgatgctggtgaagaaagcctgcactgaggaggctgtcagcctgggtttg
aatcccctcatttggaatataatcttggcaaagtctgaaagcctcaattgctcgtttgta
aaactggaagatagtaggacttgctgcccggggtcggggcaggatggaggggggcccatga
gaattaaggcagagcccagcggagtgcattgtaaggatccatgagtgtgaaccttcgttt
ttactactgcatatgaggatcctgccaacaaacctggcggcttcaagcatccttgccctt
aaccaaataagctcttaggtcctaga_ggcaggaagacttccttgaagaggcgcgggaggc_       81bp Del
_tggtgaggggagtggaggacgctctgggaccctctgggggtggggcg_ggcggggtgaact
tgaccccaggccgcgtgccgggcgtgccatctgccgctccgctgcaaggtctcgcccggg
accggggctggcggagcgcgcgcccgcgagtaggggccgggccggggaccccgcctaggc
ggcggcggccgggtccccaaggctgggcgctgcttgcggaaccgacggggcggagaggag
cgtggcgggaggaggagtaggagaaggggctggtcaagggaagtgcgacgtgtctgcgg
agcctttttatacctccttcccgggagtccggcAGCCGCTGCTGCTGCTGCTGCTGCTGC     VNTR
TGCCGCCGCCGCCGCCGTCCCTGCGTCCTTCGGTCTCTGCTCCCGGGACCCGGGCTC         Exon 1
CGCCGCAGCCAGCCAGCATGTCGGGGATCAAGAAGCAAAAGACGgtaggcttccaggcgc
cggcttccctccccgccaccgcactgcacgcgccgacccccaaccccccaattccccggca
cttgggtcccaccctccccggagggggcgtcggg_aggaggagtaagagtggggcacg_gga
gggaagcaagagaaagaggctctgtgtggaattcccggggcagtcctcgccccgcagccc
ctct (SEQ ID NO:1)
_ctatattagaatggacaaaggtgagtctctttcaaaatatttttatataagttgttaca_
_tgtatcagtttcgcaattaaaagtttaagatggatttatattggctccagtgaagaatat_
_gtgttttattaattaat_actgtgcttggttttgtcttattttatagGAGAACCAGCAGAA
ATCCACCAATGTAGTCTATCAGGCCCACCATGTGAGCAGGAATAAGAGAGGGCAAGTGGT        Exon 2
TGGAACAAGGGGTGGGTTCCGAGGATGTACCGTGTGGCTAACAGgtatgtcatgttca_ta_
_tatatatatata_caaatt_g_caaactgacatgtgacacaatttatggaaattagtgtaac
gtattacatgcttgttttatcattagaaggaggctgggagatgtagtagaaagcctgggt
gt_tagtcctaacccctaccatcagtgagaaatagagt_caaggtcaactacagaaataagag
tctg (SEQ ID NO:2)
taagtacttgccttgtagtcaactacactgatttctttctttcttttttttttttttt_aag_
_atttagttatatttaaaattactagattagttcacaatttgtcatcttaaactatccagg_
ccgatgtcagtctgttttatctgttctgaacagGTCTCTCTGGTGCTGGAAAAACAACGA
TAAGTTTTGCCCTGGAGGAGTACCTTGTCTCCCATGCCATCCCTTGTTACTCCCTGGATG
GGGACAATGTCCGTCATGGCCTTAACAGAAATCTCGGATTCTCTTCCTGGGGACAGAGAGG       Exon 3
AAAATATCCGCCGGATTGCTGAGGTGGCTAAGCTGTTTGCTGATGCTGGTCTGGTCTGCA
TTACCAGCTTTATTTCTCCATTCGCAAAGgtaaaaaaaaaaaaaaaaaaaaaaaaaaaa
aaaaaaaaaaaaaaaaggcactacacacgattcccacac_acagtgcaagtgctctccaa_
ctgctaggggaaggaatcggagagggagggcataagaatgtctcctttcaatttcccgac
tatttcttcccccaataacaggctctctcatttcctctatttaatattggttatataaag
gagttccttccttccagatgccagggcaccagtagacataaaccccttccatgttcacaa
ttataaggaacatttggtgagagtcgaagggaagagaaagttaaacaagagaaactctaa
acctctgtaatttagttgtcggaaaaaggatctagttaaagaaaagagcagttcatggc
caaagcttcgggttctatgtgtttaatgctgacatcactgaggtggagtgtcactcttct
```

FIGURE 1 – page 2

```
tttaaatcaggaaatttctgggagccaaacatcagatgtagcttagaacacatcctttga
atgaaatgctcccatatggccagtgctttcctgctaagagggcctattttccatgatttt
ctgtgaaagtccttgagagagctgtgtttaccagagtaaaatttctggactttctctcaa
gcactctgcaaagcacaaacccagtgttatctcaaggctattgaaaaccaaagtacaca
gtgttttgtgatttagaatttcaccgtgaaacctcttttacattcttaatcatattgct
tttcagGATCGTGAGAATGCCCGCAAAATACATGAATCAGCAGGGCTGCCATTCTTTGAA
ATATTTGTAGATGCACCTCTAAATATTTGTGAAAGCAGAGACGTAAAAGGCCTCTATAAA        Exon 4
AGGGCCAGAGCTGGGAGATTAAAGgtaagagaattggctagtagcgtctaccagttaca
taggctgtcagtcctcagtccttattctgtcctcagaaatcttccttgagtttcaaactg
ttttccaaaattgcatataacatgcacaacttttattagatcatgatatattcagtatg
cccagaggcttattaaaaggtagggttttattttaagaattgtcatctcagccatatgc
aataacgttcagagaactagaatggatatttatatgtgagtgtgtgtgtagaggagtg
tttcagagttcttccttattcttgtcttccttttgattgtaatcatctatagagggctt
caacttagccagcgggatttgttgacaatttggggctttccatattgaaaatacagcta
tatattttcttacttatggctagaagtcaaggatggctgtttgacctttctgttaaagt
gtgaattttcagtttaatacattattccaacatgtgttttgccttattgattaaaaagat
tattctgtcaatacagatgcgatgattgtcacccatatgctttgcagGATTTACAGGTAT
TGATTCTGATTATGAGAAACCTGAAACTCCTGAGCGTGTGCTTAAAACCAATTTGTCCAC        Exon 5
AGTGAGTGACTGTGTCCACCAGGTAGTGGAACTTCTGCAAGAGCAGgtaggtgaaccggt
tgtcttttttatatgtttaataaaatcatgaaagacaatctatgcctctttactgaagc
attcttttacagttttcaagttttaccaatgctgtttcatttcagAACATTGTACCCT
ATACTATAATCAAAGATATCCACGAACTCTTTGTGCCGGAAAACAAACTTGACCACGTCC        Exon 6
GAGCTGAGGCTGAAACTCTCCCTTCATTATCAATTACTAAGgtaagtgggtgcagactgg
tcaaataattaggcttaatatcagtcattataatttatttacaattactcttaacaataa
gaaaagtataaataaggtgcacataatgtccataaataaaacactccttttttttccaagt
tatttttaacctcttctccaaagaaatctctcaccaagaattgccacaaggcagctgatc
aatgccatgtatggaggtgactgggaaaataacttctgtatttgcattggacaatttttac
atagctgtcattgtaccagtaagtacatctggtagaaaaatatagccagaccaggatttt
tgtggataaaagaaagaaagaataaacagtgaattttcaactcagttgcacattttggga
atagatacaacctaaaaatgttcaaataagtcatctcaatacaaaatcttttcaccacta
tttcataggaaacttccaaacttaaatatttctggcccttagatcatgggttagcataac
aggtggggacacttaaaacatagaaggttctgccctcatcctcctgttaactgaataaga
aaggacttccctggggccagatgcctggaaaacagaacttatgaaaatgttcaactactt
tttgtgttttgcagCTGGATCTCCAGTGGGTCCAGGTTTTGAGCGAAGGCTGGGCCACTC
CCCTCAAAGGTTTCATGCGGGAGAAGGAGTACTTACAGGTTATGCACTTTGACACCCTGC        Exon 7
TAGATGgtatgttttgttgttgtttcttactctttgttgttaaggaaaaaaaaaatctt
tcccagaagttttgcaggaacaggaagttagtctttggtttgcaaatcttattgcaaaac
tatttggatcatttacagtgtgctccattctattatgtttaagcttccattttaggatt
ttttggttgttctcaaaggttgttcc (SEQ ID NO:3)
cccttcaaggacttgtcattatagaatctagagaaactggtgcagctaacacaactactt
ggatttgggtcttaatgcttcttgaaggaaatgtttggaaggggcattgtgcacatttga
ttcatgcttcaaggatggcacaccttatatctagttttcgtgcatcacatggctctttcc
```

FIGURE 1 – page 3

```
acagATGGCGTGATCAACATGAGCATCCCCATTGTACTGCCCGTCTCTGCAGAGGATAAG
ACACGGCTGGAAGGGTGCAGCAAGTTTGTCCTGGCACATGGTGGACGGAGGGTAGCTATC      Exon 8
TTACGAGACGCTGAATTCTATGAACACAGAAAAGAGGAACGCTGTTCCCGTGTTTGGGGG
ACAACATGTACAAAACACCCCCATATCAAAgtaagtcacaaaacctttggaaggactttc
ttgagctatttaaactgagaagaaaaataactcttttttaattcctttgcaaaggacttag
aaaaactgggattaggtggaagaatgtatttctaaggtagtgtttgcaggctttgcctca
ggagatgttttagaaaggtgcaaagaaatgtctttctgtttgaggtctg (SEQ ID NO:4)
ggtactcaataatttttaagagcataacgggttctagagaccaaaaagtttgagaaata
ctgtgccagaaatactaaagaactgaaggcagttctttaactgtaacccgagattggtct
aaaaggagaaaacttttcagataaaatagaaatcacaattaatcattagcaatcataaca
atgttctttctagATGGTGATGGAAAGTGGGGACTGGCTGGTTGGTGGAGACCTTCAGGT
GCTGGAGAAAATAAGATGGAATGATGGGCTGGACCAATACCGTCTGACACCTCTGGAGCT      Exon 9
CAAACAGAAATGTAAAGAAATGAATGCTGgtatgtaaactgttcttagtgcatttattt
atttatttattgagatggtgtcttgttctgtcacccaggctggagtgcaatggcacgatc
tcagctcactgcaacctctgcctcccaggttcaagtaattctcctgcctcagcctcctga
gtagcttggattacaggtgcccaccaccacgcccagctaattttttgtat (SEQ ID NO:5)
aggcggaggttgcagtgacctgagatcgctgactgcactccagcctgggcaacagagtga
gactctttcaaaaaaaaaaaagccagtggataatgaatgcacagaacaataaacatagc
tgtgtcctttctgttcttgtggagaaatgacaccatgtgtttctgtgaccttccttcttc
tgctttcctctcccagATGCGGTGTTTGCATTCCAGTTGCGCAATCCTGTCCACAATGGC
CATGCCCTGTTGATGCAGGACACCTGCCGCAGGCTCCTAGAGAGGGGCTACAAGCACCCG
GTCCTCCTACTACACCCTCTGGGCGGCTGGACCAAGGATGACGATGTGCCTCTAGACTGG      Exon 10
CGGATGAAGCAGCACGCGGCTGTGCTCGAGGAAGGGGTCCTGGATCCCAAGTCAACCATT
GTTGCCATCTTTCCGTCTCCCATGTTATATGCTGGCCCCACAGAGgtgagcaattcccag
agctgggctttgagactcaggaattcagactcagactttacatagaagagtaaatgagtc
tctgggatcctttctgtttcctcatgagcagattctggaatgttctggtgtctcttcttt
atctagcttaattatgtttccacttagtatttgaaaagtgctagaaggccaggcgcagtg
gctgt (SEQ ID NO:6)
cctacctaatataacaaagcatgaagagtgcacggagtcttagaacctcagtgattttct
tgcaattcttagttgactcacattgctgaattacttttaaagtagaataaaggtgtctcc
ataaaccatgacctacagatttgacccacaatgaccagcatgtcccttatggacattttc
tagGTCCAGTGGCACTGCAGGTCCGGATGATTGCGGGTGCCAATTTCTACATTGTGGGG
AGGGACCCTGCAGGAATGCCCCATCCTGAAACCAAGAAGGATCTGTATGAACCCACTCAT      Exon 11
GGGGGCAAGGTCTTGAGCATGGCCCCTGGCCTCACCTCTGTGGAAATCATTCCATTCCGA
GTGGCTGCCTACAACAAAGCCAAAAAAGCCATGGACTTCTATGATCCAGCAAGgtaggtt
ttcagaggaaaattcttttatcaacatctgtataaaagaaatgatgaggcagaatttggg
cccttttgaaaaactctccagtgcattgccacatgctcccaagtggactgagtcccttgag
agtcaagacgtggtcttataaattttatgtccctaaaattgtactacagtcttctgcat
atagtagatggtccataaatatttctctttcaacatgcattcttgagcatgcacagagtg
cctggcacactaagtgaaaggaagcaacatagaaagagattgcaatgaatatttatggtg
cacttgctcctcatgctgagggttcacagaagtaggcagagaaacagaagacagactctg
ggctcaagacacttcccaggaacagtataggcgcatggcaaatactaaatggatagctgc
```

FIGURE 1 – page 4

```
cattatttcccttctcttctgcaagttcctgaagatttagaggactgcccacttttgaag
atgcagcattttacagaaagaacatgggtctcaaaaaccataacctactccaggaatcct
taaggcagatatcatttacctacactgagttctttgttgccaccctgtaacagGCACAAT
GAGTTTGACTTCATCTCAGGAACTCGAATGAGGAAGCTCGCCCGGGAAGGAGAGAATCCC
CCAGATGGCTTCATGGCCCCCAAAGCATGGAAGGTCCTGACAGATTATTACAGGTCCCTG      Exon 12
GAGAAGAACTAAGCCTTTGGGTCCAGAGTTTCTTTCTGAAGTGCTCTTTGATTACCTTTT
CTATTTTTATGATTAGATGCTTTGTATTAAATTGCTTCTCAATGATGCATTTTAATCTTT
TATAATGAAGTAAAAGTTGTGTCTATAATTAAAAAAAATATATATATATATACACACACA
CATATACATACAAAGTCAAACTGAAGACCAAATCTTAGCAGGTAAAAGCAATATTCTTAT
ACATTTCATAATAAAATTAGCTCTATGTATTTTCTACTGCACCTGAGCAGGCAGGTCCCA
GATTTCTTAAGGCTTTGTTTGACCATGTGTCTAGTTACTTGCTGAAAAGTGAATATATTT
TCCAGCATGTCTTGACAACCTGTACTCTTCCAATGTCATTTATCAGTTGTAAAATATATC
AGATTGTGTCCTTCTTCTGTACAATTGACAAAAAAAAATTTTTTTTTCTCACTCTAAAAG
AGGTGTGGCTCACATCAAGATTCTTCCTGATATTTTACCTCATGCTGTACAAGCCTTAAT
GTGTAATCATATCTTACGTGTTGAAGACCTGACTGGAGAAACAAAATGTGCAATAACGTG
AATTTTATCTTAGAGATCTGTGCAGCCTAGATTTTACCTCATGCTGTACAAAGCCTTAAT
GTTGTAATCATATCTTACGTGTTGAGACCTGACTGGAGAAACAAAATGTGCAATAACGTG
AATTTTATCTTAGAGATCTGTGCAGCCTATTTTCTGTCACAAAAGTTATATTGTCTAATA
AGAGAAGTCTTAATGGCCTCTGTGAATAATGTAACTCAGTTACACGGTGACTTTTAATAG
CATACAGTGATTTGATGAAAGGACGTCAAACAATGTGGCGATGTCGTGGAAAGTTATCTT
TCCCGCTCTTTGCTGTGGTCATTGTGTCTTGCAGAAAGGATGGCCCTGATGCAGCAGCAG
CGCCAGCTGTAATAAAAAATAATTCACACTATCAGACTAGCAAGGCACTAGAACTGGAAA
AGACCACAGAAAACAAAGAATCCAACCCTTTCATCTTACAGGTGAACAAACTGTGATGAT
GCACATGTATGTGTTTTGTAAGCTGTGAGCACCGTAACAAAATGTAAATTTGCCATTATT
AGGAAAGTGCTGGTGGCAGTGAAGAAGCACCCAGGCCACTTGACTCCCAGTCTGGTGCCC
TGTCTACACCAGACAACACAGGAGCTGGGTCAGATTCCCCTCAGCTGCTTAACAAAGTTC
CTCGAACAGAAAGTGCTTACAAAGCTGCCTTCTCGGATACTGAAAGGTCGAGTTTTCTGA
ACTGCACTGATTTTATTGCAGTTGAAAAAAAAAAAGCTATTCCAAAGATTTCAAGCTGTT
CTGAGACATCTTCTGATGGCTTTACTTCCTGAGAGGCAATGTTTTTACTTTATGCATAAT
TCATTGTTGCCAAGGAATAAAGTGAAGAAACAGCACCTTTTAATATATAGGTCTCTCTGG
AAGAGACCTAAATTAGAAAGAGAAAACTGTGACAATTTTCATATTCTCATTCTTAAAAAA
CACTAATCTTAACTAACAAAAGTTCTTTTGAGAATAAGTTACACACAATGGCCACAGCAG
TTTGTCTTTAATAGTATAGTGCCTATACTCATGTAATCGGTTACTCACTACTGCCTTTAA
AAAAAAAACCAGCATATTTATTGAAAACATGAGACAGGATTATAGTGCCTTAACCGATA
TATTTTGTGACTTAAAAAATACATTTAAAACTGCTCTTCTGCTCTAGTACCATGCTTAGT
GCAAATGATTATTTCTATGTACAACTGATGCTTGTTCTTATTTTAATAAATTTATCAGAG
TGAAggctgagttttttctgcctgtaccattgggtgtgggttgaccacacaacttaaggg
Ctttgtgactttgtataattggagtgagacagcagcaactctcttgaacatcataactga
gattatttacccttattcatgtcttttttatttttttatttttttaaagacgaagtcttg
ctctgtcacccaggctggagtgctgtggcacgatctcggct (SEQ ID NO:7)
```

FIGURE 2A

```
1     ctgctgccgc cgccgccgcc gccgtccctg cgtccttcgg tctctgctcc cgggacccgg
61    ctccgccgca gccagccagc atgtcgggga tcaagaagca aaagacggag aaccagcaga
121   aatccaccaa tgtagtctat caggcccacc atgtgagcag gaataagaga gggcaagtgg
181   ttggaacaag gggtgggttc cgaggatgta ccgtgtggct aacaggtctc tctggtgctg
241   gaaaaacaac gataagtttt gccctggagg agtaccttgt ctcccatgcc atcccttgtt
301   actccctgga tggggacaat gtccgtcatg gccttaacag aaatctcgga ttctctcctg
361   gggacagaga ggaaaatatc cgccggattg ctgaggtggc taagctgttt gctgatgctg
421   gtctggtctg cattaccagc tttatttctc cattcgcaaa ggatcgtgag aatgcccgca
481   aaatacatga atcagcaggg ctgccattct ttgaaatatt tgtagatgca cctctaaata
541   tttgtgaaag cagagacgta aaaggcctct ataaagggc cagagctggg gagattaaag
601   gatttacagg tattgattct gattatgaga aacctgaaac tcctgagcgt gtgcttaaaa
661   ccaatttgtc cacagtgagt gactgtgtcc accaggtagt ggaacttctg caagagcaga
721   acattgtacc ctatactata atcaaagata tccacgaact ctttgtgccg gaaaacaaac
781   ttgaccacgt ccgagctgag gctgaaactc tcccttcatt atcaattact aagctggatc
841   tccagtgggt ccaggttttg agcgaaggct gggccactcc cctcaaaggt ttcatgcggg
901   agaaggagta cttacaggtt atgcactttg acccctgct agatgatggc gtgatcaaca
961   tgagcatccc cattgtactg cccgtctctg cagaggataa gacacggctg gaagggtgca
1021  gcaagtttgt cctggcacat ggtggacgga gggtagctat cttacgagac gctgaattct
1081  atgaacacag aaaagaggaa cgctgttccc gtgtttgggg gacaacatgt acaaaacacc
1141  cccatatcaa aatggtgatg aaagtgggg actggctggt tggtggagac cttcaggtgc
1201  tggagaaaat aagatggaat gatgggctgg accaataccg tctgacacct ctggagctca
1261  aacagaaatg taaagaaatg aatgctgatg cggtgtttgc attccagttg cgcaatcctg
1321  tccacaatgg ccatgccctg ttgatgcagg acacctgccg caggctccta gagagggct
1381  acaagcaccc ggtcctccta ctacaccctc tgggcggctg gaccaaggat gacgatgtgc
1441  ctctagactg gcggatgaag cagcacgcgg ctgtgctcga ggaaggggtc ctggatccca
1501  agtcaaccat tgttgccatc tttccgtctc ccatgttata tgctggcccc acagaggtcc
1561  agtggcactg caggtcccgg atgattgcgg tgccaatttt ctacattgtg gggagggacc
1621  ctgcaggaat gccccatcct gaaaccaaga aggatctgta tgaacccact catggggca
1681  aggtcttgag catggcccct ggcctcacct ctgtggaaat cattccattc cgagtggctg
1741  cctacaacaa agccaaaaaa gccatggact ctatgatcc agcaaggcac aatgagtttg
1801  acttcatctc aggaactcga atgaggaagc tcgcccggga aggagagaat ccccagatg
1861  gcttcatggc ccccaaagca tggaaggtcc tgacagatta ttacaggtcc ctggagaaga
1921  actaagcctt tgggtccaga gtttctttct gaagtgctct ttgattacct tttctatttt
1981  tatgattaga tgctttgtat taaattgctt ctca (SEQ ID NO:8)
```

FIGURE 2B

MSGIKKQKTENQQKSTNVVYQAHHVSRNKRGQVVGTRGGFRGCTVWLTGLSGAGKTT
ISFALEEYLVSHAIPCYSLDGDNVRHGLNRNLGFSPGDREENIRRIAEVAKLFADAGLVCI
TSFISPFAKDRENARKIHESAGLPFFEIFVDAPLNICESRDVKGLYKRARAGEIKGFTGIDS
DYEKPETPERVLKTNLSTVSDCVHQVVELLQEQNIVPYTIIKDIHELFVPENKLDHVRAE
AETLPSLSITKLDLQWVQVLSEGWATPLKGFMREKEYLQVMHFDTLLDDGVINMSIPIV
LPVSAEDKTRLEGCSKFVLAHGGRRVAILRDAEFYEHRKEERCSRVWGTTCTKHPHIKM
VMESGDWLVGGDLQVLEKIRWNDGLDQYRLTPLELKQKCKEMNADAVFAFQLRNPV
HNGHALLMQDTCRRLLERGYKHPVLLLHPLGGWTKDDDVPLDWRMKQHAAVLEEGV
LDPKSTIVAIFPSPMLYAGPTEVQWHCRSRMIAGANFYIVGRDPAGMPHPETKKDLYEP
THGGKVLSMAPGLTSVEIIPFRVAAYNKAKKAMDFYDPARHNEFDFISGTRMRKLARE
GENPPDGFMAPKAWKVLTDYYRSLEKN (SEQ ID NO:9)

3'-PHOSPHOADENOSINE - 5'-PHOSPHOSULFATE SYNTHETASE 2 (PAPSS2) SEQUENCE VARIANTS

CROSS-REFERENCE TO RELATED APPLICATIONS

This application claims priority from U.S. Provisional Application Ser. No. 60/332,685, filed Nov. 14, 2001.

STATEMENT AS TO FEDERALLY SPONSORED RESEARCH

Funding for the work described herein was provided in part by the federal government under grant nos. R01 GM28157, R01 GM35720, and UO1 GM61388. The federal government may have certain rights in the invention.

TECHNICAL FIELD

The invention relates to PAPSS2 nucleic acid and amino acid sequence variants.

BACKGROUND

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which, in mammals, is divided into two families, SULT1 or phenol SULTs and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) subfamilies. SULT2 subfamilies include two hydroxysteroid SULTs, 2A1 and 2B1.

Sulfotransferases use 3'-phosphoadenosine 5'-phosphosulfate (PAPS) as a sulfate donor during sulfate conjugation reactions. PAPS is synthesized from ATP and inorganic sulfate by PAPS synthetase (PAPSS). Two PAPSS genes, PAPSS1 and PAPSS2, have been identified in humans. Xu et al., *Biochem. Biophys. Res. Commun.* (2000) 268(2):437–444. The PAPSS1 cDNA is approximately 2.7 kb in length and was mapped to human chromosome band 4q24 by fluorescence in situ hybridization (FISH) analysis. The PAPSS2 cDNA is approximately 4.2 kb in length and was mapped to 10q22–23 by FISH.

SUMMARY

The invention is based on the discovery of sequence variants that occur in both coding and non-coding regions of PAPSS2 nucleic acids. Certain PAPSS2 nucleotide sequence variants encode PAPSS2 enzymes that are associated with individual differences in enzymatic activity. Other PAPSS2 sequence variants in non-coding regions of the PAPSS2 nucleic acid may alter regulation of transcription and/or splicing of the PAPSS2 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of PAPSS2 sequence variants also allows predisposition to joint diseases, hormone dependent diseases, or cancer to be assessed in individuals.

In one aspect, the invention features an isolated nucleic acid molecule containing a PAPSS2 nucleic acid sequence, wherein the nucleic acid molecule is at least ten nucleotides in length. The PAPSS2 nucleic acid sequence can contain a nucleotide sequence variant at a position selected from the group consisting of: a) position −499, −472, −100, −77, or −30 relative to the adenine of the PAPSS2 translation initiation codon within SEQ ID NO:1; b) position 28, 276, 612, 841, 871, 1295, or 1991 relative to the adenine of the PAPSS2 translation initiation codon within SEQ ID NO:8; c) position −33 or −103 relative to the guanine in the splice acceptor site of intron 1 within SEQ ID NO:2; d) position 27 or 35 relative to the guanine in the splice donor site of intron 2 within SEQ ID NO:2; e) position −41 relative to the guanine in the splice acceptor site of intron 3 within SEQ ID NO:3; f) position 21 or 133 relative to the guanine in the splice donor site of intron 4 within SEQ ID NO:3; g) position −28 or −149 relative to the guanine in the splice acceptor site of intron 4 within SEQ ID NO:3; h) position 4 relative to the guanine in the splice donor site of intron 6 within SEQ ID NO:3; i) position 17 relative to the guanine in the splice donor site of intron 7 within SEQ ID NO:3; j) position −34, −70, or −99 relative to the guanine in the splice acceptor site of intron 7 within SEQ ID NO:4; and k) position 96 relative to the guanine in the splice donor site of intron 9 within SEQ ID NO:5. The nucleotide sequence variant can be a nucleotide substitution, a nucleotide insertion, or a nucleotide deletion.

The nucleotide sequence variant can be selected from the group consisting of an adenine substitution for guanine at position 28 relative to the adenine of the PAPSS2 translation initiation codon, a thymine substitution for adenine at position 841 relative to the adenine of the PAPSS2 translation initiation codon, an adenine substitution for guanine at position 871 relative to the adenine of the PAPSS2 translation initiation codon, and an adenine substitution for guanine at position 1295 relative to the adenine of the PAPSS2 translation initiation codon. The nucleotide sequence variant can be a cytosine substitution for thymine at position 276 relative to the adenine of the PAPSS2 translation initiation codon, or a thymine substitution for cytosine at position 612 relative to the adenine of the PAPSS2 translation initiation codon. The nucleotide sequence variant at position −33 or 103 relative to the guanine in the splice acceptor site of intron 1 can be a deletion of the sequence 5'-TAAT-3' at position −33 or a thymine substitution for adenine at position −103.

The nucleotide sequence variant at position 27 or 35 relative to the guanine in the splice donor site of intron 2 can be an insertion of the sequence 5'-AT-3' at position 27, an insertion of the sequence 5'-ATAT-3' at position 27, or an adenine substitution for guanine at position 35. The nucleotide sequence variant at position −41 relative to the guanine in the splice acceptor site of intron 3 can be an adenine substitution for guanine. The nucleotide sequence variant at position 21 or 133 relative to the guanine in the splice donor site of intron 4 can be an adenine substitution for cytosine at position 21 or a cytosine substitution for thymine at position 133. The nucleotide sequence variant at position −28 or −149 relative to the guanine in the splice acceptor site of intron 4 can be a thymine substitution for cytosine at position −28 or an adenine substitution for guanine at position −149. The nucleotide sequence variant at position 4 relative to the guanine in the splice donor site of intron 6 can be a cytosine substitution for adenine. The nucleotide sequence variant at position 17 relative to the guanine in the splice donor site of intron 7 can be an adenine substitution for guanine. The nucleotide sequence variant at position −34, −70, or −99 relative to the guanine in the splice acceptor site of intron 7 can be a guanine substitution for cytosine at position −34, a guanine substitution for adenine at position −70, or a guanine substitution for adenine at position −99. The nucleotide sequence variant at position 96 relative to the guanine in the splice donor site of intron 9 can be a thymine substitution for cytosine. The nucleotide sequence variant at position −499, −472, −100, −77, −30 relative to the adenine of the PAPSS2 translation initiation codon can be a cytosine substitution for thymine at position −499, an insertion of the sequence 5'-GGCAGGAAGACT-TCCTTGAAGAGGCGCGGGAGGCTGGTGAGGGG AGTGGAGGACGCTCTGGGAC-CCTCTGGGGGTGGGGCG-3' (SEQ ID NO:10) at position −472, a deletion of one or two 5'-GCT-3' repeats at position −100, an insertion of one, two, three, or four 5'-GCT-3' repeats at position −77, or an adenine substitution for guanine at position −30. The nucleotide sequence variant at position 1991 relative to the adenine of the PAPSS2 translation initiation codon can be an adenine substitution for thymine.

The PAPSS2 nucleic acid sequence can contain at least two nucleotide sequence variants (e.g., one or more variants at position 17 relative to the guanine in the splice donor site of intron 7 and position 1991 relative to the adenine of the PAPSS2 translation initiation codon).

In another aspect, the invention features an isolated nucleic acid encoding a PAPSS2 polypeptide, wherein the polypeptide contains a PAPSS2 amino acid sequence variant relative to the amino acid sequence of SEQ ID NO:9. The amino acid sequence variant can be at a residue selected from the group consisting of 10, 281, 291, and 432 (e.g., a lysine at residue 10, a leucine at residue 281, a methionine at residue 291, and a lysine at residue 432).

The invention also features an isolated PAPSS2 polypeptide, wherein the polypeptide contains a PAPSS2 amino acid sequence variant relative to the amino acid sequence of SEQ ID NO:9. The amino acid sequence variant can be at a residue selected from the group consisting of 10, 281, 291, and 432 (e.g., a lysine at residue 10, a leucine at residue 281, a methionine at residue 291, and a lysine at residue 432). Activity of the polypeptide can be altered relative to a wild type PAPSS2 polypeptide.

In another aspect, the invention features an isolated nucleic acid molecule containing a PAPSS2 nucleic acid sequence, wherein the nucleic acid molecule is at least ten nucleotides in length, and wherein the PAPSS2 nucleic acid sequence has at least 99% sequence identity to a region of SEQ ID NO:2, SEQ ID NO:3, SEQ ID NO:4, or SEQ ID NO:6. Nucleotide 28 relative to the adenine of the PAPSS2 translation initiation codon can be an adenine, nucleotide 841 relative to the adenine of the PAPSS2 translation initiation codon can be a thymine, nucleotide 871 relative to the adenine of the PAPSS2 translation initiation codon can be an adenine, or nucleotide 1295 relative to the adenine of the PAPSS2 translation initiation codon can be an adenine, The region can be selected from the group consisting of: a) nucleotides 28 to 100 of SEQ ID NO:2 relative to the adenine of the PAPSS2 translation initiation codon; b) nucleotides 800 to 900 of SEQ ID NO:3 relative to the adenine of the PAPSS2 translation initiation codon; c) nucleotides 865 to 925 of SEQ ID NO:4 relative to the adenine of the PAPSS2 translation initiation codon; and d) nucleotides 1250 to 1350 of SEQ ID NO:6 relative to the adenine of the PAPSS2 translation initiation codon.

In yet another aspect, the invention features an article of manufacture including a substrate, wherein the substrate includes a population of isolated PAPSS2 nucleic acid molecules, and wherein the nucleic acid molecules include a PAPSS2 nucleotide sequence variant. The substrate can include a plurality of discrete regions, wherein each region includes a different population of isolated PAPSS2 nucleic acid molecules, and wherein each population of molecules includes a different PAPSS2 nucleotide sequence variant.

The invention also features a method for determining if a mammal is predisposed to a joint disease. The method includes obtaining a biological sample from a mammal, and detecting the presence or absence of a PAPSS2 nucleotide sequence variant in the sample, wherein predisposition to a joint disease is determined based on the presence or absence of a variant. The method can also include detecting the presence or absence of a plurality of PAPSS2 nucleotide sequence variants in the sample to obtain a variant profile of the mammal, wherein predisposition to a joint disease is determined based on the variant profile.

In another aspect, the invention features a method for determining if a mammal is predisposed to cancer. The method includes obtaining a biological sample from a mammal, and detecting the presence or absence of a PAPSS2 nucleotide sequence variant in the sample, wherein predisposition to cancer is determined based on the presence or absence of a variant. The method can also include detecting the presence or absence of a plurality of PAPSS2 nucleotide sequence variants in the sample to obtain a variant profile of the mammal, and wherein predisposition to cancer is determined based on the variant profile. The cancer can be a chemically induced cancer.

The invention also features a method for assisting a medical or research professional. The method includes obtaining a biological sample from a mammal, and detecting the presence or absence of a plurality of PAPSS2 nucleotide sequence variants in the sample to obtain a variant profile of the mammal. The method can also include communicating the profile to the medical or research professional.

In yet another aspect, the invention features an isolated nucleic acid molecule including a PAPSS2 nucleic acid sequence, wherein the nucleic acid molecule is at least ten nucleotides in length, and wherein the PAPSS2 nucleic acid sequence includes at least two nucleotide sequence variants. The variants can be within any combination of coding sequences, intron sequences, 5' untranslated sequences, or 3' untranslated sequences. For example, the variants can be selected from the group consisting of one or more variants at positions −30, −77, −100, −472, −499, or 1991 relative to the adenine of the PAPSS2 translation initiation codon, a variant at position −33 or −103 relative to the guanine in the splice acceptor site of intron 1, a variant at position 27 or 35 relative to the guanine in the splice donor site of intron 2, a variant at position −41 relative to the guanine in the splice acceptor site of intron 3, a variant at position 21 or 133 relative to the guanine in the splice donor site of intron 4, a variant at position −28 or −149 relative to the guanine in the splice acceptor site of intron 4, a variant at position 4 relative to the guanine in the splice donor site of intron 6, a variant at position 17 relative to the guanine in the splice donor site of intron 7, a variant at position −34, −70, or −99 relative to the guanine in the splice acceptor site of intron 7, or a variant at position 96 relative to the guanine in the splice donor site of intron 9.

The variants can include one of more variants at positions 28, 841, 871, or 1295 relative to the adenine of the PAPSS2 translation initiation codon. The variants can also include one or more variants at positions 276 or 612 relative to the adenine of the PAPSS2 translation initiation codon. Further, one of the variants can include a variant at position 1991 relative to the adenine of the PAPSS2 translation initiation codon. In addition, the variants can be at position 17 relative to the guanine in the splice donor site of intron 7 and position 1991 relative to the adenine of the PAPSS2 translation initiation codon.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleotide sequence of the reference PAPSS2 (SEQ ID NOS: 1–7). Single nucleotide polymorphisms (SNPs) are indicated in underlined italics, exons are in uppercase, introns are in lowercase, coding regions are in boldface, and primer sequences are indicated by thick underlines.

FIG. 2A is a cDNA sequence (SEQ ID NO:8) containing the ORF of the reference PAPSS2 (nucleotides 81 to 1925). FIG. 2B is the amino acid sequence (SEQ ID NO:9) of the reference PAPSS2.

DETAILED DESCRIPTION

Figure 3:
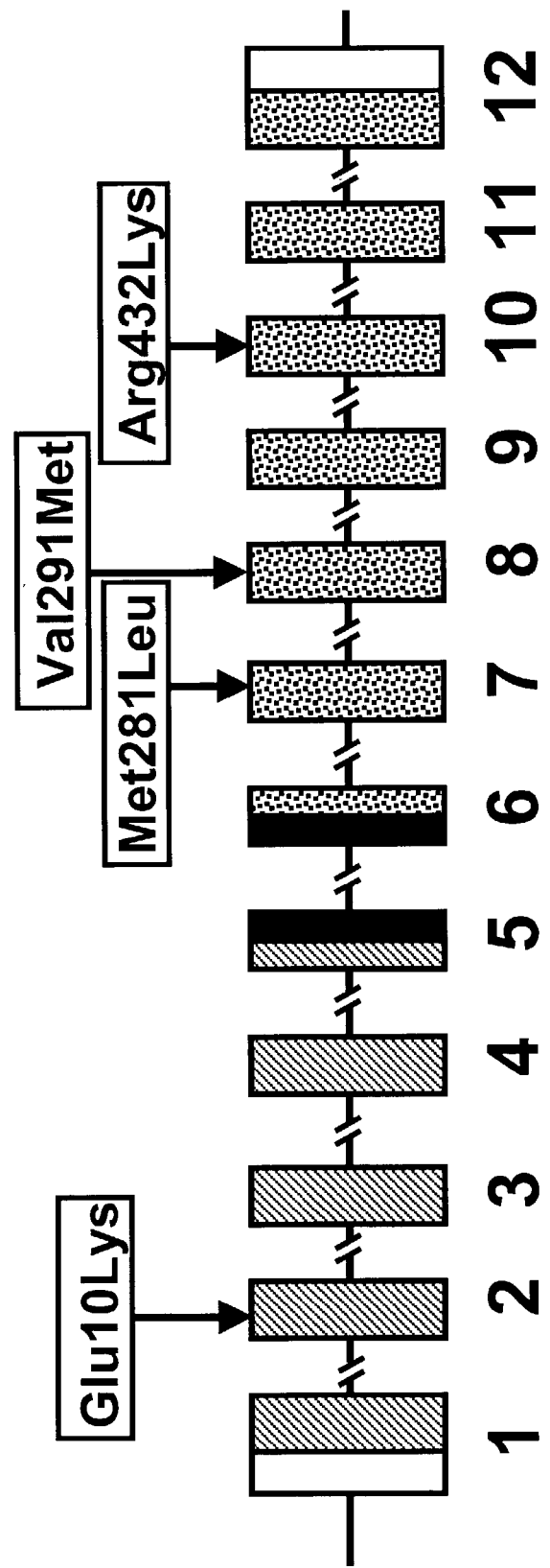
FIG. 3 is a schematic of the location of the non-synonymous polymorphisms within the PAPSS2 amino acid sequence.

The invention features PAPSS2 nucleotide and amino acid sequence variants. PAPSS2 is one of two enzymes that synthesize PAPS, the high energy sulfate donor used in the sulfate conjugation of thousands of drugs, hormones (e.g., estrogen), neurotransmitters (e.g., dopamine), and other endogenous compounds. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. Sulfation of certain compounds, however, such as the hydroxy metabolite of 2-acetylaminofluorene (AAF), produces sulfate conjugates that are chemically unstable and that can degrade to form reactive, electrophilic species. In particular, sulfation of the hydroxy metabolite of AAF produces a reactive N—O-sulfate ester, which can rearrange and fragment into a reactive electrophilic species that can bind to nucleic acids and proteins. Thus, detecting PAPSS nucleic acid and amino acid sequence variants can facilitate the prediction of therapeutic efficacy and toxicity of drugs on an individual basis, as well as the ability to biotransform certain hormones and neurotransmitters. Furthermore, inactivation of the PAPSS gene results in severe, early degenerative arthritis. Thus, detecting PAPSS nucleic acid and amino acid variants can be used to determine predisposition to joint diseases such as osteoarthritis.

Nucleic Acid Molecules

The invention features isolated nucleic acids that include a PAPSS2 nucleic acid sequence. The PAPSS2 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-PAPSS2 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10–20 (e.g., 11, 12, 13, 14, 15, 16, 17, 18, 19, or 20 nucleotides in length), 20–50, 50–100 or greater than 100 nucleotides in length (e.g., greater than 150, 200, 250, 300, 350, 400, 450, 500, 750, or 1000 nucleotides in length). Nucleic acids of the invention can be in a sense or antisense orientation, can be complementary to the PAPSS2 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187–195; and Hyrup et al. (1996) *Bioorgan. Med. Chem.* 4(1):5–23. In addition, the deoxyphosphate backbone can be replaced with, for example, a phosphorothioate or phosphorodithioate backbone, a phosphoramidite, or an alkyl phosphotriester backbone.

As used herein, "nucleotide sequence variant" refers to any alteration in a PAPSS2 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference PAPSS2 nucleic acid sequence is provided in FIG. 1 (SEQ ID NO:1) and in GenBank (Accession Nos. AF160503–AF160509). The reference PAPSS2 cDNA including the PAPSS2 ORF is provided in FIG. 2A (SEQ ID NO:2) and the corresponding reference PAPSS2 amino acid sequence is provided in FIG. 2B (SEQ ID NO:3). The mRNA and amino acid reference sequences also are found in GenBank (Accession No. AF091242). The nucleic acid and amino acid reference sequences also are referred to herein as "wild type."

As used herein, "untranslated sequence" includes 5' and 3' flanking regions that are outside of the mRNA as well as 5' and 3' untranslated regions (5'-UTR or 3'-UTR) that are part of the mRNA, but are not translated. Positions of nucleotide sequence variants in 5' untranslated sequences are designated as "–X" relative to the "A" in the translation initiation codon; positions of nucleotide sequence variants in the coding sequence and 3' untranslated sequence are designated as "+X" or "X" relative to the "A" in the translation initiation codon. Nucleotide sequence variants that occur in introns are designated as "+X" or "X" relative to the "G" in the splice donor site (GT) or as "–X" relative to the "G" in the splice acceptor site (AG).

In some embodiments, a PAPSS2 nucleotide sequence variant encodes a PAPSS2 polypeptide having an altered amino acid sequence. The term "polypeptide" refers to a chain of at least four amino acid residues (e.g., 4–8, 9–12, 13–15, 16–18, 19–21, 22–100, 100–150, 150–200, 200–300 residues, or a full-length PAPSS2 polypeptide). PAPSS2 polypeptides may or may not have PAPSS catalytic activity, or may have altered activity relative to the reference PAPSS2 polypeptide. Polypeptides that do not have activity or have altered activity are useful for diagnostic purposes (e.g., for producing antibodies having specific binding affinity for variant PAPSS polypeptides).

Corresponding PAPSS2 polypeptides, irrespective of length, that differ in amino acid sequence are herein referred to as allozymes. For example, a PAPSS2 nucleic acid sequence that includes an adenine at nucleotide 28 encodes a PAPSS2 polypeptide having a lysine at amino acid residue 10. This polypeptide (Glu10Lys) would be considered an allozyme with respect to the reference PAPSS2 polypeptide that contains a glutamic acid at amino acid residue 10. Additional non-limiting examples of PAPSS2 sequence variants that alter amino acid sequence include variants at nucleotides 841, 871, and 1295. For example, a PAPSS2 nucleic acid molecule can include a thymine at nucleotide 841 and encode a PAPSS2 polypeptide having a leucine at amino acid residue 281 in place of a methionine residue (Met281 Leu); an adenine at nucleotide 871 and encode a PAPSS2 polypeptide having a methionine at amino acid 291 in place of a valine (Val291Met); or an adenine at nucleotide 1295 and encode a PAPSS2 polypeptide having a lysine at amino acid 432 in place of an arginine (Arg432Lys).

PAPSS2 allozymes as described above are encoded by a series of PAPSS alleles. These alleles represent nucleic acid sequences containing sequence variants, typically multiple sequence variants, within coding and non-coding sequences. Representative examples of single nucleotide variants are described above. Table 2 sets out a series of PAPSS2 alleles that encode PAPSS2. Some alleles are commonly observed, i.e., have an allele frequency>1%, such as alleles encoding Val291Met. The relatively large number of alleles and allozymes for PAPSS2 indicates the potential complexity of PAPSS pharmacogenetics. Such complexity emphasizes the need for determining single nucleotide variants, (i.e., single nucleotide polymorphisms, SNPs) as well as complete PAPSS2 haplotypes (i.e., the set of alleles on one chromosome or a part of a chromosome) of patients.

Certain PAPSS2 nucleotide sequence variants do not alter the amino acid sequence. Such variants, however, could alter regulation of transcription as well as mRNA stability. PAPSS2 variants can occur in intron sequences, for example, within introns 1, 2, 3, 4, 5, 6, 7, 8, 9, 10, or 11. In particular, the nucleotide sequence variant can include a deletion of a 4 bp sequence (5'-TAAT-3') at nucleotide –33, or a thymine substitution at nucleotide –103 of intron 1. Intron 2 variants can include an insertion of "AT" at 27, a deletion of a 4 bp sequence (5'-ATAT-3') at nucleotide 27, or substitution of an adenine at nucleotide 35. Intron 3 variants can include an adenine substitution at nucleotide –41. Intron 4 sequence variants can include an adenine substitution at nucleotide 21, a cytosine substitution at nucleotide 133, an adenine substitution at nucleotide –149, or a thymine substitution at nucleotide –28. Intron 6 sequence variants can include a cytosine substitution at nucleotide 4. Intron 7 variants can include an adenine substitution at nucleotide 17, a guanine substitution at nucleotide –99, a guanine substitution at nucleotide –70, or a guanine substitution at nucleotide –34. Intron 9 sequence variants can include a thymine substitution at nucleotide 96.

PAPSS2 nucleotide sequence variants that do not change the amino acid sequence also can be within an exon or in 5' or 3' untranslated sequences. For example, the 5' flanking region of PAPSS2 can include a cytosine substitution at nucleotide –499, or a deletion of 81 bp (5'-GGCAGGAA-GACTTCCTTGAAGAGGCGCGGGAGGCTGGTG AGGGGAGTGGAGGACGCTCTGGGAC-CCTCTGGGGGTGGGGCG-3', SEQ ID NO:4) at nucleotide –472, and the 5' UTR can include an insertion of 1–4 (i.e., 1, 2, 3, or 4) trinucleotide repeats (5'-GCT-3') at nucleotide –77, or a deletion of 1 or 2 trinucleotide repeats (5'-GCT-3') at nucleotide –100. The 3' UTR can contain an adenine substitution at nucleotide 1991.

In some embodiments, nucleic acid molecules of the invention can have at least 90% (e.g., 91%, 92%, 95%, 98%, 98.5%, 99.0%, 99.5%, 99.6%, 99.7%, 99.8%, 99.9%, or 100%) sequence identity with a region of SEQ ID NO:1, SEQ ID NO:2, SEQ ID NO:3, SEQ ID NO:4, SEQ ID NO:5, SEQ ID NO:6, or SEQ ID NO:7 that includes one or more variants described herein. The region of SEQ ID NO: 1, 2, 3, 4, 5, 6, or 7 is at least ten nucleotides in length (e.g., ten, 15, 20, 50, 60, 70, 75, 100, 150 or more nucleotides in length). For example, a nucleic acid molecule can have at least 90% identity with a region of SEQ ID NO:1 containing nucleotides –550 to –450, –500 to –400, –150 to –50, or –75 to 25 relative to the adenine of the PAPSS2 translation initiation codon, where the nucleotide sequence of SEQ ID NO:1 includes one or more of the variants described herein. For example, the nucleotide sequence of SEQ ID NO:1 can have a cytosine at nucleotide –499 relative to the adenine of the PAPSS2 translation initiation codon, an 81 base pair deletion between nucleotides −472 and −392 relative to the adenine of the PAPSS2 translation initiation codon, an insertion or deletion of one or more guanine-cytosine-thymine repeats between nucleotides −100 and −77 relative to the adenine of the PAPSS2 translation initiation codon, or an adenine at nucleotide −30 relative to the adenine of the PAPSS2 translation initiation codon, and combinations thereof. In another embodiment, a nucleic acid molecule can have at least 99% identity with a region of SEQ ID NO:2 containing nucleotides −150 to −50 or −75 to −1 relative to the guanine in the splice acceptor site of intron 1, nucleotides 28 to 100 relative to the adenine of the PAPSS2 translation initiation codon, or nucleotides 1 to 75 relative to the guanine in the splice donor site of intron 2, where the nucleotide sequence of SEQ ID NO:2 includes one or more of the variants described herein. For example, the nucleotide sequence of SEQ ID NO:2 can have a thymine at nucleotide −103 or a four base pair deletion between nucleotides −33 and −30 relative to the guanine of the splice acceptor site of intron 1, an adenine at nucleotide 28 relative to the adenine of the PAPSS2 translation initiation codon, an insertion of one or more adenine-thymine repeats at nucleotide 27 relative to the guanine in the splice donor site of intron 2, or an adenine at nucleotide 35 relative to the guanine in the splice donor site of intron 2, and combinations thereof.

In another embodiment, a nucleic acid molecule can have at least 99% identity with a region of SEQ ID NO:3 containing nucleotides 225 to 325, 575 to 675, or 800 to 900 relative to the adenine of the PAPSS2 translation initiation codon, nucleotides −75 to −1 relative to the guanine in the splice acceptor site of intron 3, nucleotides 1 to 75 or nucleotides 80 to 175 relative to the guanine in the splice donor site of intron 4, nucleotides −200 to −100 or −75 to −1 relative to the guanine in the splice acceptor site of intron 4, nucleotides 1 to 50 relative to the guanine in the splice donor site of intron 6, or nucleotides 1 to 50 relative to the guanine in the splice donor site of intron 7, where the nucleotide sequence of SEQ ID NO:3 includes one or more of the variants described herein. For example, the nucleotide sequence of SEQ ID NO:3 can have a cytosine at nucleotide 276, a thymine at nucleotide 612, or a thymine at nucleotide 841 relative to the adenine of the PAPSS2 translation initiation codon, an adenine at nucleotide −41 relative to the guanine of the splice acceptor site of intron 3, an adenine at nucleotide 21 or a cytosine at nucleotide 133 relative to the guanine in the splice donor site of intron 4, an adenine at nucleotide −149 or a thymine at nucleotide −28 relative to the guanine in the splice acceptor site of intron 4, a cytosine at nucleotide 4 relative to the guanine in the splice donor site of intron 6, or an adenine at nucleotide 17 relative to the guanine in the splice donor site of intron 7, and combinations thereof.

In yet another embodiment, a nucleic acid molecule can have at least 99% identity with a region of SEQ ID NO:4 containing nucleotides −150 to −50 or −75 to −1 relative to the guanine in the splice acceptor site of intron 7, or nucleotides 865 to 925 relative to the adenine of the PAPSS2 translation initiation codon, where the nucleotide sequence of SEQ ID NO:4 includes one or more of the variants described herein. For example, the nucleotide sequence of SEQ ID NO:4 can have a guanine at nucleotide −99, a guanine at nucleotide −70, or a guanine at nucleotide −34 relative to the guanine in the splice acceptor site of intron 7, or an adenine at nucleotide 871 relative to the adenine of the PAPSS2 translation initiation codon, and combinations thereof. In another embodiment, a nucleic acid molecule can have at least 99% identity with a region of SEQ ID NO:5 containing nucleotides 50 to 150 relative to guanine in the splice donor site of intron 9, where the nucleotide sequence of SEQ ID NO:5 includes one or more of the variants described herein. For example, the nucleotide sequence of SEQ ID NO:5 can have a thymine at nucleotide 96 relative to the guanine in the splice donor site of intron 9. In yet another embodiment, a nucleic acid molecule can have at least 99% identity with a region of SEQ ID NO:6 containing nucleotides 1250 to 1350 relative to the adenine of the PAPSS2 translation initiation codon, where the nucleotide sequence of SEQ ID NO:6 includes one or more of the variants described herein. For example, the nucleotide sequence of SEQ ID NO:6 can have an adenine at nucleotide 1295 relative to the adenine of the PAPSS2 translation initiation codon. In another embodiment, a nucleic acid molecule can have at least 99% identity with a region of SEQ ID NO:7 containing nucleotides 1950 to 2050 relative to the adenine of the PAPSS2 translation initiation codon, where the nucleotide sequence of SEQ ID NO:7 includes one or more of the variants described herein. For example, the nucleotide sequence of SEQ ID NO:7 can have an adenine at nucleotide 1991 relative to the adenine of the PAPSS2 translation initiation codon.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (www.fr.com/blast) or the U.S. government's National Center for Biotechnology Information web site (www.ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. The following command will generate an output file containing a comparison between two sequences: C:\Bl2seq −i c:\seq1.txt −j c:\seq2.txt −p blastn −o c:\output.txt −q−1−r2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO: 1, (2) the B12seq program presents 969 nucleotides from the target sequence aligned with a region of the sequence set forth in SEQ ID NO: 1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100 =93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a PAPSS2 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis *Genetic Engineering News*, 12(9):1 (1992); Guatelli et al., *Proc. Natl. Acad. Sci. USA*, 87:1874–1878 (1990); and Weiss, *Science*, 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequences depicted in FIG. 1 or 2A can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified are described above.

PAPSS2 Polypeptides

Isolated PAPSS2 polypeptides of the invention include an amino acid sequence variant relative to the reference PAPSS2 (FIG. 2B, GenBank Accession No. AF091242). The term "isolated" with respect to a PAPSS2 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

PAPSS2 polypeptides of the invention include variants at one or more of residues 10, 281, 291 and 432. In particular, a lysine residue can be substituted at position 10, a leucine residue at position 281, a methionine at position 291, or a lysine at position 432.

In some embodiments, activity of PAPSS2 polypeptides is altered relative to the reference PAPSS2. As described herein, certain PAPSS2 allozymes have reduced activity (e.g., Val291Met and Glu10Lys), while other allozymes (e.g., Met281Leu and Arg432Lys) have activity that is comparable to the reference PAPSS2. Other allozymes can have increased activity relative to the reference PAPSS2. Activity of PAPSS2 polypeptides can be assessed in vitro. For example, recombinant PAPSS2 polypeptides can be used to generate PAPS from ATP and inorganic sulfate. The activity of PAPSS2 polypeptides can then be indirectly assessed by determining the amount of sulfated 17 β-[$^3$H] estradiol that is produced by a recombinant sulfotransferase (e.g., recombinant SULT1E1) in the presence of the generated PAPS. See, Xu et al. *Drug. Metab. Dispos.* (2001) 29(2):172–178.

Other biochemical properties of allozymes, such as apparent $K_m$ values, also can be altered relative to a reference PAPSS2. Apparent $K_m$ values can be calculated, for example, by using the method of Wilkinson with a computer program written by Cleland. Wilkinson, *Biochem. J.*, 80:324–332 (1961); and Cleland, *Nature*, 198:463–365 (1963).

Isolated polypeptides of the invention can be obtained, for example, by extraction from a natural source (e.g., liver tissue), chemical synthesis, or by recombinant production in a host cell. To recombinantly produce PAPSS2 polypeptides, a nucleic acid encoding a PAPSS2 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a PAPSS nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express PAPSS2 variant polypeptides. For example, BL-21 cells can be transformed with a pGEX vector containing a PAPSS2 nucleic acid sequence. The transformed bacteria can be grown exponentially and then stimulated with isopropylthiogalactopyranoside (IPTG) prior to harvesting. In general, the PAPSS2-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed PAPSS2 polypeptide can be released from the GST moiety.

In eukaryotic host cells, a number of viral-based expression systems can be utilized to express PAPSS2 variant polypeptides. A nucleic acid encoding a polypeptide of the invention can be cloned into, for example, a baculoviral vector such as pBlueBac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Eukaryotic cell lines that stably express PAPSS2 variant polypeptides can be produced using expression vectors with the appropriate control elements and a selectable marker. For example, the eukaryotic expression vector pCR3.1 (Invitrogen) and p91023(B) (see Wong et al., *Science* (1985) 228: 810–815) or modified derivatives thereof are suitable for expression of PAPSS2 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (Invitrogen, San Diego, Calif.) and then transcribed and translated in vitro using wheat germ extract or rabbit reticulocyte lysate.

PAPSS2 variant polypeptides can be purified by known chromatographic methods including DEAE ion exchange, gel filtration, and hydroxylapatite chromatography. See, for example, Flohe et al., *Biochim. Biophys. Acta*, (1970) 220: 469–476; and Tilgmann et al., *FEBS* (1990) 264:95–99. PAPSS2 polypeptides can be "engineered" to contain a tag sequence describe herein that allows the polypeptide to be purified (e.g., captured onto an affinity matrix). Immunoaffinity chromatography also can be used to purify PAPSS2 polypeptides.

Non-Human Mammals

The invention features non-human mammals that include PAPSS2 nucleic acids of the invention, as well as progeny and cells of such non-human mammals. Non-human mammals include, for example, rodents such as rats, guinea pigs, and mice, and farm animals such as pigs, sheep, goats, horses, and cattle. Non-human mammals of the invention can express a PAPSS2 variant nucleic acid in addition to an endogenous PAPSS2 (e.g., a transgenic non-human that includes a PAPSS2 nucleic acid randomly integrated into the genome of the non-human mammal). Alternatively, an endogenous PAPSS2 nucleic acid can be replaced with a PAPSS2 variant nucleic acid of the invention by homologous recombination. See, Shastry, *Mol. Cell Biochem.*, (1998) 181(1–2):163–179, for a review of gene targeting technology.

In one embodiment, non-human mammals are produced that lack an endogenous PAPSS2 nucleic acid (i.e., a knockout), and then a PAPSS2 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous PAPSS2 nucleic acid. That is, cultured ES cells can be transformed with a knockout construct and cells selected in which the PAPSS2 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37–9.52 of Sambrook et al., *Molecular Cloning, A Laboratory Manual*, second edition, Cold Spring Harbor Press, Plainview; NY, 1989.

To generate a knockout animal, ES cells having at least one inactivated PAPSS2 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated PAPSS2 allele. If the original ES cell was heterozygous for the inactivated PAPSS2 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the PAPSS2 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous PAPSS2 gene and express a PAPSS2 nucleic acid of the invention, and then fused with enucleated oocytes. After activation of the oocytes, the eggs are cultured to the blastocyst stage, and implanted into a recipient. See, Cibelli et al., *Science*, (1998) 280:1256–1258. Adult somatic cells, including, for example, cumulus cells and mammary cells, can be used to produce animals such as mice and sheep, respectively. See, for example, Wakayama et al., *Nature*, (1998) 394(6691):369–374; and Wilmut et al., *Nature*, (1997) 385(6619):810–813. Nuclei can be removed from genetically modified adult somatic cells, and transplanted into enucleated oocytes. After activation, the eggs can be cultured to the 2–8 cell stage, or to the blastocyst stage, and implanted into a suitable recipient. Wakayama et al., 1998, supra.

Non-human mammals of the invention such as mice can be used to screen, for example, toxicity of compounds that are substrates for PAPSS2, drugs that alter PAPSS2 activity, or for carcinogenesis. For example, PAPSS2 activity or toxicity can be assessed in a first group of such non-human mammals in the presence of a compound, and compared with PAPSS2 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting PAPSS2 Sequence Variants

PAPSS2 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33–39), denaturing high performance liquid chromatography (DHPLC, Underhill et al., 1997, *Genome Res.*, 7:996–1005), infrared matrix-assisted laser desorption/ionization (IR-MALDI) mass spectrometry (WO 99/57318), and combinations of such methods.

Genomic DNA generally is used in the analysis of PAPSS2 nucleotide sequence variants. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the PAPSS2 gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al., 1991, *Am. J. Hum. Genet.* 48:370–382; and Prince et al., 2001, *Genome Res.*, 11(1): 152–162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For PAPSS2 sequence variants that do not alter a common restriction site, mutagenic primers can be designed that introduce a restriction site when the variant allele is present or when the wild type allele is present. A portion of PAPSS2 nucleic acid can be amplified using the mutagenic primer and a wild type primer, followed by digest with the appropriate restriction endonuclease.

Certain variants, such as insertions or deletions of one or more nucleotides (e.g., deletion of an 81 bp sequence in the 5'-FR), change the size of the DNA fragment encompassing the variant. The insertion or deletion of nucleotides can be assessed by amplifying the region encompassing the variant and determining the size of the amplified products in comparison with size standards. For example, a region of PAPSS2 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163–169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, PAPSS2 variants can be detected by antibodies that have specific binding affinity for variant PAPSS2 polypeptides. Variant PAPSS2 polypeptides can be produced in various ways, including recombinantly, as discussed above. Host animals such as rabbits, chickens, mice, guinea pigs, and rats can be immunized by injection of a PAPSS2 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a PAPSS2 variant polypeptide and standard hybridoma technology. In particular, monoclonal antibodies can be obtained by any technique that provides for the production of antibody molecules by continuous cell lines in culture such as described by Kohler et al., Nature, 256:495 (1975), the human B-cell hybridoma technique (Kosbor et al., Immunology Today, 4:72 (1983); Cole et al., Proc. Natl. Acad. Sci USA, 80:2026 (1983)), and the EBV-hybridoma technique (Cole et al., Monoclonal Antibodies and Cancer Therapy, Alan R. Liss, Inc., pp. 77–96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a PAPSS2 variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., Science, 246: 1275 (1989). Once produced, antibodies or fragments thereof are tested for recognition of PAPSS variant polypeptides by standard immunoassay methods including ELISA techniques, radioimmunoassays and Western blotting. See, Short Protocols in Molecular Biology, Chapter 11, Green Publishing Associates and John Wiley & Sons, edited by Ausubel et al., 1992.

Methods of the Invention

As a result of the present invention, it is now possible to determine PAPS synthesis status of a mammal (e.g., a human subject) as well as to determine if particular SNPs are linked to a particular disease or clinical condition. In some embodiments, for example, it is possible to determine whether a mammal is predisposed (i.e., has a relative greater risk) to joint diseases, hormone dependent diseases, or cancer. "PAPS synthesis status" refers to the ability of a mammal to synthesize PAPS. Additional risk factors including, for example, family history and other genetic factors can be considered when determining risk. Predisposition to joint diseases, hormone dependent diseases, or cancer can be determined based on the presence or absence of a single PAPSS2 sequence variant or based on a variant profile. "Variant profile" refers to the presence or absence of a plurality (i.e., two or more sequence variants) of PAPSS2 nucleotide sequence variants or PAPSS2 amino acid sequence variants. For example, a variant profile can include the complete PAPSS2 haplotype of the mammal or can include the presence or absence of a set of common non-synonymous SNPs (i.e., single nucleotide substitutions that alter the amino acid sequence of a PAPSS2 polypeptide). In one embodiment, the variant profile includes detecting the presence or absence of two or more non-synonymous SNPs (e.g., 2, 3, 4 or more non-synonymous SNPs) described above. There may be ethnic-specific pharmacogenetic variation, as certain of the nucleotide and amino acid sequence variants described herein were detected solely in a particular ethnic group (i.e., a group of African-American subjects or a group of Caucasian subjects). In addition, the variant profile can include detecting the presence or absence of any type of PAPSS2 SNP together with any other PAPSS2 SNP (i.e., a polymorphism pair or groups of polymorphism pairs). Such polymorphism pairs include, without limitation, those pairs described in Table 3. Further, the variant profile can include detecting the presence or absence of any PAPSS SNP together with any SNP from another PAPSS. For example, a variant profile can include SNPs from both PAPSS1 and PAPSS2.

Articles of Manufacture

Articles of manufacture of the invention include populations of isolated PAPSS2 nucleic acid molecules or PAPSS2 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different PAPSS2 nucleic acid or PAPSS2 polypeptide sequence variant. Such articles of manufacture can include two or more sequence variants of PAPSS2, or can include all of the sequence variants known for PAPSS2. Furthermore, nucleic acid molecules containing sequence variants for other PAPS synthetases, such as PAPSS1, can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., Nature Genet., 14:441–447 (1996); and U.S. Pat. Nos. 5,770,722 and 5,733,729.

The invention will be further described in the following examples, which do not limit the scope of the invention described in the claims.

EXAMPLES

Example 1

Methods and Materials

PCR Amplification and DNA Sequencing: The Polymorphism Discovery Resource 90 DNA sample subset (Collins et al., Genome Res., 8:1229–1231 (1998)) was obtained from the Coriell Cell Repository (Camden, N.J.) and was used to resequence human PAPSS2. These DNA samples had been both individually and ethnically anonymized, but the sample set had been structured to reflect the ethnic diversity present in the United States. Written informed consent was obtained from all donors for the use of their DNA for this purpose, and the experiments disclosed herein were reviewed and approved by the Mayo Clinic Institutional Review Board.

Specifically, 13 PCR amplifications were performed with each DNA sample to make it possible to amplify all PAPSS2 exons and splice junctions as well as approximately 500 base pairs of the 5'-flanking region. Dye-primer DNA sequencing chemistry was used to facilitate the identification of heterozygous bases (Chadwick et al., *Biotechniques*, 20:676–683 (1996)). In order to use dye primer chemistry, M13 sequencing primers were added to the 5'-ends of each forward and reverse primer. All forward primers contained the M13 forward sequence (5'-TGTAAAACGACGGC-CAGT-3'; SEQ ID NO: 12), and all reverse primers contained the M13 reverse sequence (5'-CAGGAAACAGC-TATGACC-3'; SEQ ID NO:13). Locations of all primers were chosen to avoid repetitive sequence as well as regions of known homology between the genes that encode the two PAPSS isoforms. Primers were designed to have relatively high $T_m$ values so amplifications could be performed at high annealing temperatures (64–66° C.). Specifically, the annealing temperature was 66° C. for all amplifications except those for the 5'-FR (64° C.) and for exon 3 (60° C.). Primer sequences and locations are listed in Table 1. "F" represents forward; "R", reverse; "U", upstream; "D", downstream; "I", intron; "FR", flanking region; and "UTR", untranslated region.

Reactions were performed with AmpliTaq Gold DNA polymerase (Perkin Elmer, Foster City, Calif.) with a "hot start" to help ensure amplification specificity. Since the 5'-flanking region, exon 1 and intron 1 of the human PAPSS2 gene are GC-rich, 5% DMSO was added to those reactions. Amplicons were sequenced in the Mayo Molecular Biology Core Facility with an ABI 377 DNA sequencer using Big-Dye™ (Perkin Elmer) dye primer sequencing chemistry. Both strands were sequenced except for the exon 1, 3, and 7 reaction products. In those cases, the presence of either polymorphic repetitive sequence or long nucleotide homopolymers prevented the sequencing of both strands. To exclude random PCR-induced artifacts, an independent amplification was performed for those DNA samples in which a SNP was observed only once among the 90 samples studied.

DNA sequence chromatograms were analyzed using the PolyPhred 3.0 (Nickerson et al., *Nucl. Acids Res.*, 25:2745–2751 (1997)) and Consed 8.0 (Gordon et al., *Genome Res.*, 8:195–202 (1998)) programs obtained from the University of Washington. The University of Wisconsin GCG software package, Version 10, also was used to analyze nucleotide sequence. The GenBank accession numbers for the PAPSS2 reference sequences used to perform these analyses were AF160503 to AF160509.

COS-1 Cell Expression: Five different PAPSS2 expression constructs were made using a loxP-modified p91023(B) acceptor expression vector. Four of the constructs were designed to express variant PAPSS2 polypeptides, while the remaining construct was designed to express a wild type PAPSS2. All PAPSS2 cDNA sequences used to create the expression constructs were created by site directed mutagenesis using the method described by Ho et al., *Gene* 77(1): 51–9 (1989). The loxP-modified p91023(B) acceptor expression vector was generated by ligating a PCR-amplified 133 bp fragment from pcDNA4/HisMax-E (nucleotides 1080–1212; Invitrogen, Carlsbad, Calif.) containing an N-terminal His-tag and a loxP site into the EcoRI site of p91023(B) (Wong et al., *Science* (1985) 228:810–815).

Expression constructs and expression of recombinant allozymes: The Echo™ cloning system (Invitrogen) was chosen to create expression constructs for the wild-type PAPSS2 allele as well as the 4 non-synonymous cSNPs observed during the resequencing studies. The size of the pUni/V5-His-TOPO (pUni) donor vector used in this expression system (2.3 kb) is well suited for performing "circular PCR" during site-directed mutagenesis. Specifically, the wild-type full-length open reading frame (ORF) of the human PAPSS2 cDNA (GenBank accession number AF091242) was amplified using human adrenal Marathon-Ready cDNA (Clontech) as the template with primers F1 (5'-ATGTCGGGGATCAAGAAGCAAAAGACG-3'; SEQ ID NO:14) and R1848 (5'-GGCTTAGTTCTTCTCCAGG-GACCT-3'; SEQ ID NO:15). R1848 was designed to include the stop codon present in the cDNA (underlined in the primer sequence) so the C-terminal His tag in the pUni vector would not be attached to the insert of interest. The amplicon obtained from this reaction was subcloned into the pUni donor vector.

Initial expression studies were performed with the commercially available pcDNA4/HisMax-E (pcDNA4) acceptor vector (Invitrogen). Specifically, the pUni donor vector, with and without the PAPSS2 cDNA insert, was combined with the pcDNA4 acceptor vector by Cre recombinase through the loxP sites present in both donor and acceptor vectors. The resultant fusion constructs (pUni/pcDNA4) then were used to transfect either COS-1 or HepG2 cells. However, the construct with the wild type PAPSS2 cDNA insert expressed only about 2-fold higher PAPSS activity in both COS-1 and HepG2 cells than did the control "empty" pUni-pcDNA4. This low signal/noise ratio was due in part to the high levels of endogenous PAPSS activity in mammalian cells. Obviously, this situation would have made it difficult to study the functional significance of PAPSS2 non-synonymous cSNPs.

The loxP site required for Cre recombinase-mediated recombination thus was adapted for cloning into the p91023 (b) cloning site so a recombination approach could be used to clone PAPSS2 cDNAs into this vector. A 133 base pair pcDNA4 DNA segment (nucleotides 1080–1212) containing the N-terminal His-tag and the loxP site was amplified by PCR, and this amplicon was ligated into the EcoRI site of p91023(b). As a result, the loxP-modified p91023(b) acceptor vector was also able to add an N-terminal His-tag to the expressed protein. In order to assure that the His-tag did not alter enzyme function, both the loxP-modified p91023(b) and "unmodified" p91023(b) were tested as expression vectors in selected experiments.

Variant alleles of the four non-synonymous PAPSS2 cSNPs observed during the resequencing experiments were created using the QuickChange Site-Directed Mutagenesis Kit (Stratagene, La Jolla, Calif.), with wild type PAPSS2 cDNA in pUni as template. The sequence of the pUni insert was confirmed by completely sequencing both strands before recombination with the loxP-modified p91023(b) acceptor vector. pUni donor vectors that contained wild type and variant PAPSS2 cDNAs, as well as empty pUni, then were combined with the loxP-modified p91023(b) acceptor vector to generate the final expression constructs. In all cases, the fusion junctions of resultant expression constructs were sequenced to confirm that the construct was a dimer consisting of only a single donor and a single acceptor vector. These expression constructs were used to transfect COS-1 cells using TransFast™ reagent (Promega) with a 1:1 charge ratio. pSV-β-galactosidase (Promega) was co-transfected with each construct as an internal control to correct for transfection efficiency. Transfected COS-1 cells were harvested after 48 hours and were homogenized with a Polytron homogenizer (Brinkmann Instruments, Westbury, N.Y.) in 25 mM potassium phosphate buffer, pH 7.8, containing 1 mM dithiothreitol (DTT) and 1 mM EDTA. The homogenates were centrifuged at 15,000 g for 15 minutes, and the resultant supernatant preparations were used to perform enzyme assays, substrate kinetic studies and Western blot analyses. In some cases, aliquots of these cytosol preparations were stored at −80° C. prior to assay.

PAPSS2 Enzyme Activity: PAPSS2 activity was measured with a coupled radiochemical assay. See Xu et al., 2001, supra. Briefly, PAPS is generated from ATP and Na$_2$SO$_4$ in a PAPSS2-catalyzed reaction. The generated PAPS is then used as a substrate for the SULT1E1-catalyzed sulfate conjugation of [2,4,6,7-$^3$H]estradiol, a radioactively labeled sulfate acceptor substrate. The cell homogenate preparations of recombinant PAPSS2 allozymes described above were used for the activity studies without any further purification. The protein concentration of each recombinant protein preparation was determined by the dye-binding method of Bradford with bovine serum albumin (BSA) as a standard.

PAPS synthesis was catalyzed by recombinant wild-type PAPSS2 or PAPSS2 allozymes (present in the cell homogenate preparations described above) in the presence of 1 mM ATP, 16 mM Na$_2$SO$_4$, 1 mM MgCl$_2$, and 2 mM DTT in 60 mM glycine-NaOH buffer, pH 8.6. Blank samples included the same quantity of COS-1 cytosol protein from cells that had been transfected with empty expression vector to make it possible to correct for endogenous activity. Reaction mixtures were incubated at 37° C. for 20 minutes, and then terminated by heating at 100° C. for 1 minute. An aliquot from this PAPS-generating reaction was then added to a second, coupled reaction containing recombinant human SULT1E1 isolated from COS-1 cells transfected with a SULT1E1 expression construct (see Aksoy et al., *Biochem. Biophys. Res. Commun.*, 200:1621–1629 (1994)). The coupled reaction also included 27 nM [2,4,6,7-$^3$H]estradiol, 8 mM DTT and 1.25 mM MgCl$_2$ in 10 mM potassium phosphate buffer, pH 6.5. The second, SULT1E1-catalyzed reactions were incubated at 37° C. for 20 minutes, and then terminated by the addition of KOH, followed by organic solvent extraction performed with chloroform. Radioactivity of the sulfate conjugated [2,4,6,7-$^3$H]estradiol in the aqueous phase after organic solvent extraction was then measured in a liquid scintillation counter. PAPSS activities of recombinant PAPSS2 allozymes were compared after correction for transfection efficiency by measuring the activity of cotransfected β-galactosidase. β-Galactosidase activity in the COS-1 cell preparations was measured with the β-Galactosidase Assay System (Promega) as described by the manufacturer.

To estimate apparent K$_m$ values of PAPSS2 for the two reaction cosubstrates, a series of ATP (0.125–4 mM) and Na$_2$SO$_4$ (0.125–16 mM) concentrations were tested with the recombinant allozymes. When ATP was the varied substrate, the concentration of Na$_2$SO$_4$ was 4 mM, and when Na$_2$SO$_4$ was the varied substrate, the concentration of ATP was 1 mM. Blanks for each substrate concentration were included by assaying COS-1 cell cytosol after transfection with empty vector. These data were fitted to a series of kinetic models, and the most appropriate model was selected on the basis of the dispersion of residuals and a determination of whether the F-test showed a significant reduction (P<0.05) in the residual sums of squares.

Western Blot Analysis: Quantitative Western blot analysis was performed with recombinant PAPSS2 allozymes after expression in COS-1 cells. Since all constructs included an N-terminal His-tag, we used anti-His monoclonal antibodies (Invitrogen) to measure levels of immunoreactive PAPSS2 protein with the ECL detection system (Amersham Pharmacia, Piscataway, N.J.). The quantity of COS-1 cell preparation loaded on the gel for each allozyme was adjusted to achieve equal quantities of β-galactosidase activity, i.e., gel loading was adjusted to correct for transfection efficiency. The AMBIS Radioanalytic Imaging System, Quant Probe Version 4.31 (Ambis, Inc., San Diego, Calif.) was used to quantitate immunoreactive protein in each lane, and those data were expressed as a percentage of the intensity of the wild type PAPSS2 band on the gel.

Data Analysis: Apparent K$_m$ values were calculated by using the method of Wilkinson with a computer program written by Cleland. Wilkinson, *Biochem. J.*, 80:324–332 (1961); and Cleland, *Nature*, 198:463–365 (1963). Statistical comparisons of data were performed by ANOVA with the StatView program, version 4.5 (Abacus Concepts, Inc., Berkeley, Calif.). Apparent K$_m$, S$_{50}$ and V$_{max}$ values for the wild-type and variant PAPSS2 allozymes were compared by the use of unpaired Student's t-test.

Linkage disequilibrium for PAPSS2 polymorphisms was analyzed after the DNA samples had been genotyped at each of the 26 polymorphic sites. Linkage analysis was performed using the EH program developed by Terwilliger and Ott, *Handbook of Human Genetic Linkage*, The Johns Hopkins University Press, Baltimore, pp. 188–193 (1994). D' values, a quantitative method for reporting linkage data that is independent of allele frequency (Hartl and Clark, *Principles of Population Genetics*, 3$^{rd}$ edition, Sinauer Associates, Inc. (Sunderland, Mass.), pp. 96–106 (1997); and Hedrick, Genetics of Populations, 2$^{nd}$ edition, Jones and Bartlett (Sudbury, Mass.), pp. 396–405 (2000)), were calculated. The AT repeat polymorphism in intron 2 could not be included in this analysis because it was not possible to determine accurate genotypes for all samples. In addition, a short variable number GCT tandem repeat in the 5'-UTR was excluded because it was not a biallelic polymorphism.

TABLE 1

PCR primers used or resequencing PAPSS2

| Primer Name | Primer Location | Primer Sequence (5' to 3' direction) | SEQ ID NO: |
|---|---|---|---|
| UF(-606) M13 | 5'-FR | TGTAAAACGACGGCCAGTGAGCCCAGCGGAGTGCATTGTAAG | SEQ ID NO:16 |
| UR(-122) M13 | 5'-FR | CAGGAAACAGCTATGACCAGGTATAAAAAGGCTCCGCAGACACG | SEQ ID NO:17 |
| UF(-168) M13 | 5'-FR | TGTAAAACGACGGCCAGTGCTGGTCAAGGGAAGTGCGACG | SEQ ID NO:18 |
| I1R133 M13 | Intron 1 | CAGGAAACAGCTATGACCGTGCCCCACTCTTACTCCTCCTC | SEQ ID NO:19 |
| I1F(-166) M13 | Intron 1 | TGTAAAACGACGGCCAGTCTATATTAGAATGGACAAAGGTGAGTCTCTTTCAA | SEQ ID NO:20 |
| I2R169 M13 | Intron 2 | CAGGAAACAGCTATGACCCTATTTCTCACTGATGGTAGGGTTAGGACTA | SEQ ID NO:21 |

TABLE 1-continued

PCR primers used or resequencing PAPSS2

| Primer Name | Primer Location | Primer Sequence (5' to 3' direction) | SEQ ID NO: |
|---|---|---|---|
| I2F(-96) M13 | Intron 2 | TGTAAAACGACGGCCAGTAAGATTTAGTTATATTTAAAATTACTAGATTAGTTCAC | SEQ ID NO:22 |
| I3R92 M13 | Intron 3 | CAGGAAACAGCTATGACCGTTGGAGAGCACTTGCACTGT | SEQ ID NO:23 |
| I3F(-135) M13 | Intron 3 | TGTAAAACGACGGCCAGTTTCTCTCAAGCACTCTGCAAAGCACAAAC | SEQ ID NO:24 |
| I4R178 M13 | Intron 4 | CAGGAAACAGCTATGACCCTACCTTTTAATAAGCCTCTGGGCATACTGAATA | SEQ ID NO:25 |
| I4F(-217) M13 | Intron 4 | TGTAAAACGACGGCCAGTAGCGGGATTTTGTTGACAATTTGGGGCTT | SEQ ID NO:26 |
| I5R107 M13 | Intron 5 | CAGGAAACAGCTATGACCCATTGGTAAAAACTTGAAAACTGTAAAAAGAATGCTTCAG | SEQ ID NO:27 |
| F610 M13 | Exon 5 | TGTAAACGACGGCCAGTCACCAGGTAGTGGAACTTCTGCAAGAG | SEQ ID NO:28 |
| I6R186 M13 | Intron 6 | CAGGAAAACAGCTATGACCGTGGCAATTCTTGGTGAGAGATTTCTTTGGA | SEQ ID NO:29 |
| I6F(-149) M13 | Intron 6 | TGTAAAACGACGGCCAGTATGGGTTAGCATAACAGGTGGGGAC | SEQ ID NO:30 |
| I7R158 M13 | Intron 7 | CAGGAAACAGCTATGACCGCTTAAACATAATAGAATGGAGCACACTGTAAATGAT | SEQ ID NO:31 |
| I7F(-134) M13 | Intron 7 | TGTAAAACGACGGCCAGTACAACTACTTGGATTTGGGTCTTAATGCTTCT | SEQ ID NO:32 |
| I8R117 M13 | Intron 8 | CAGGAAACAGCTATGACCACATTCTTCCACCTAATCCCAGTTTTTCTAAGT | SEQ ID NO:33 |
| I8F(-141) M13 | Intron 8 | TGTAAAACGACGGCCAGTGAGAAATACTGTGCCAGAAATACTAAAGAACTGA | SEQ ID NO:34 |
| I9R174 M13 | Intron 9 | CAGGAAACAGCTATGACCTGGGCACCTGTAATCCAAGCTACTC | SEQ ID NO:35 |
| I9F(-113) M13 | Intron 9 | TGTAAAACGACGGCCAGTCCAGTGGATAATGAATGCACAGAACAATAAAC | SEQ ID NO:36 |
| I10R101 M13 | Intron 10 | CAGGAAACAGCTATGACCCATGAGGAAACAGAAAGGATCCCAGAG | SEQ ID NO:37 |
| I10F(-122) M13 | Intron 10 | TGTAAAACGACGGCCAGTGCAATTCTTAGTTGACTCACATTGCTGAATTACTT | SEQ ID NO:38 |
| I11R131 M13 | Intron 11 | CAGGAAACAGCTATGACCGACTCTCAAGGGACTCAGTCCACTT | SEQ ID NO:39 |
| I11F(-127) M13 | Intron 11 | TGTAAAACGACGGCCAGTGCCCACTTTTGAAGATGCAGCATTTTACAG | SEQ ID NO:40 |
| R2075 M13 | 3'-UTR | CAGGAAACAGCTATGACCGTATAAGAATATTGCTTTTACCTGCTAAGATTTGGTC | SEQ ID NO:41 |

Underlined nucleotides indicate M13 tag

Example 2

PAPSS2 Sequencing and Polymorphisms

Thirteen separate PCR amplifications were performed for each of the 90 individual DNA samples studied. These resequencing experiments involved the analysis, in total, of approximately 1 million base pairs of nucleotide sequence. 84.6% of that DNA was sequenced on both strands, making it possible to verify polymorphism calls by using data from the complimentary strand. Failure to sequence both strands occurred either because of the presence of insertion/deletion events or homopolymers, both of which present significant challenges with current DNA sequencing technology. For example, exon 1 was resequenced only in the reverse direction because there was a polymorphic GCT repeat at its 5'-terminus, and exons 3 and 7 were resequenced only in the forward direction because of the presence of poly(A) tracts that were located near these exons within introns 3 and 7.

A total of 26 polymorphisms were observed in the 90 DNA samples that were resequenced, including 22 SNPs and 4 insertion/deletion events (Table 2). Polymorphisms in exons, untranslated regions (UTR), and flanking regions (FR) are numbered relative to the adenine in the PAPSS2 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is -1). Four of the 26 variations altered the encoded amino acid (i.e., a non-synonymous SNP), resulting in four different PAPSS2 allozymes. One of the four variants (frequency≧1%, Table 2) in the sample set.

Six of the SNPs were present in the coding-region (cS-NPs), and 4 cSNPs (those located in exons 2, 7, 8 and 10) were nonsynonymous, resulting in alterations in the following encoded amino acids: Glu10Lys, Met28Leu, Val291Met and Arg432Lys. Only the Val291Met polymorphism appeared to be "common", having a frequency greater than 1% (1.7%). The longest sequence variation involved an 81 base pair insertion/deletion located 286 bp upstream of the site of transcription initiation as determined by 5'-RACE (Xu et al., 2000, supra). Use of the MatInspector V2.2 program (Quandt et al., Nucl. Acids Res., 23:4878–4884 (1995)) revealed that deletion of this 81 base pair segment resulted in the loss of putative binding sites for several transcription factors including Sp1, upstream stimulating factor (USF), and signal transducer and activator of transcription (STAT; see FIG. 4). The sample containing the 81 base pair deletion was homozygous for this variant. The presence of the deletion was confirmed by performing an independent amplification, which continued to show homozygous deletion of an 81 base pair tract. We used a similar approach to confirm the presence of a variable number tandem repeat (VNTR) in the 5'-untranslated region, i.e., within exon 1, beginning 76 base pairs upstream from the "A" in the ATG translation initiation codon (FIG. 4). This VNTR had also been observed during previous 5'-RACE experiments (Xu et al., 2000, supra). Seven different VNTR alleles were observed that contained from 6 to 12 GCT trinucleotide repeats. The frequencies for 8, 9, and 11 GCT repeats were 0.606, 0.328, and 0.044 in the 90 DNA samples analyzed. Alleles with 6, 7, 10 and 12 GCT trinucleotide repeats were observed only once each. Finally, a polymorphic dinucleotide AT repeat was present in intron 2. The most frequent allele at this location contained 7 repeats, but 10 of the 90 DNA samples studied were homozygous for 9 AT repeats. Since it is technically difficult to obtain high quality sequence for heterozygous samples with polymorphic repeats, it was not possible to exclude the potential existence of additional alleles containing this repeat.

Polymorphisms that were observed only once accounted for 12 of the 26 observed. To exclude possible artifacts introduced by PCR-dependent misincorporation, independent amplifications were performed and the resulting amplicons were sequenced for all situations in which a given polymorphism was observed only once among the 90 samples studied. All 12 polymorphisms that had been observed only once were verified by this procedure.

The polymorphisms observed in PAPSS2 then were compared with data for 313 human genes recently reported by Stephens et al. (*Science*, 293:489–493 (2001)). The authors had resequenced DNA samples from 82 ethnically diverse subjects. Both the number of individual samples resequenced and the ethnic composition of the samples thus were similar to those used in the present study. Stephens et al. reported an average of 3.4 polymorphisms per kilobase in coding regions, 5.3 in 5'-UTRs, 5.9 in 5'-flanking regions and 7.0 in 3'-UTRs. Very similar values were observed for PAPSS2, with 3.2 SNPs per kilobase within the coding region and 6.0 in the UTRs and 5'-flanking region. Stephens et al. also calculated two standard measures of nucleotide diversity: π, average heterozygosity per site and θ, the population mutation parameter (Hartl and Clark, supra; and Hedrick, supra). For the 292 autosomal genes resequenced by Stephens et al., π averaged 0.058% and the average value for θ was 0.096%. The values were very similar when the same parameters were calculated for PAPSS2, with π equal to 0.037% and θ equal to 0.077%. In summary, the present observations for PAPSS2 were very similar to average values for 313 human genes reported by Stephens et al.

The SNPs observed herein also were compared with those present in publicly accessible databases. Twenty human PAPSS2 SNPs had been deposited in the SNP database (www.ncbi.nlm.nih.gov/SNP), including 16 located within introns, 2 in the 5'-flanking region, and 2 in the 3'-UTR. The 18 database SNPs within introns and the 5'-flanking region were not located in regions that were resequenced in the present studies. One (C→G at nucleotide 1854) of the two 3'-UTR-based SNPs was not observed during the present resequencing studies, but the other (T→A at nucleotide 1991) was. The human PAPSS2 cDNA ORF also was used to search the EST database, and the 50 PAPSS2 EST sequences that had been deposited in the database for the presence of polymorphisms were analyzed. Only the initial 400 bp of each EST sequence was used to assure high sequence quality. None of the 6 cSNPs disclosed herein was present in these EST sequences. In summary, only 1 of the 26 polymorphisms observed during these resequencing studies was available in public databases, and none of the cSNPs were publicly available.

TABLE 2

Human PAPSS2 sequence variants

| | | Nucleotide | | Altered | Frequency |
|---|---|---|---|---|---|
| Position | Location | Wild Type Allele | Variant Allele | Amino Acid | of Variant |
| −499 | 5'-FR | T | C | | 0.311 |
| −472 | 5'-FR | GGCAGGAAGAC TTCCTTGAAGAG GCGCGGGAGGC TGGTGAGGGGA GTGGAGGACGC TCTGGGACCCTC TGGGGGTGGGG CG (SEQ ID NO: 10) | 81 bp deletion | | 0.011 |
| −100/−77 | 5'-UTR | 8GCT repeats | GCT deletion | | 0.006 |
| −100/−77 | 5'-UTR | 8GCT repeats | *(GCT)$_2$ deletion | | 0.006 |
| −100/−77 | 5'-UTR | 8GCT repeats | GCT insertion | | 0.328 |
| −100/−77 | 5'-UTR | 8GCT repeats | (GCT)$_2$ insertion | | 0.006 |
| −100/−77 | 5'-UTR | 8GCT repeats | (GCT)$_3$ insertion | | 0.044 |
| −100/−77 | 5'-UTR | 8GCT repeats | (GCT)$_4$ insertion | | 0.006 |
| −30 | 5'-UTR | G | A | | 0.006 |
| I1(−103) | Intron 1 | A | T | | 0.022 |
| I1(−33) | Intron 1 | TAAT | 4 bp deletion | | 0.006 |
| 28 | Exon 2 | G | A | Glu10Lys | 0.006 |
| I2(27) | Intron 2 | 7 AT repeats | AT insertion | | >0.100 |
| I2(27) | Intron 2 | 7 AT repeats | ATAT insertion | | >0.100 |
| I2(35) | Intron 2 | G | A | | 0.011 |
| 276 | Exon 3 | T | C | | 0.017 |
| I3(−41) | Intron 3 | G | A | | 0.006 |
| I4(21) | Intron 4 | C | A | | 0.011 |
| I4(133) | Intron 4 | T | C | | 0.122 |
| I4(−149) | Intron 4 | G | A | | 0.006 |

TABLE 2-continued

Human PAPSS2 sequence variants

| Position | Location | Nucleotide Wild Type Allele | Nucleotide Variant Allele | Altered Amino Acid | Frequency of Variant |
|---|---|---|---|---|---|
| I4(−28) | Intron 4 | C | T | | 0.006 |
| 612 | Exon 5 | C | T | | 0.006 |
| I6(4) | Intron 6 | A | C | | 0.006 |
| 841 | Exon 7 | A | T | Met281Leu | 0.006 |
| I7(17) | Intron 7 | G | A | | 0.094 |
| I7(−99) | Intron 7 | A | G | | 0.006 |
| I7(−70) | Intron 7 | A | G | | 0.022 |
| I7(−34) | Intron 7 | C | G | | 0.011 |
| 871 | Exon 8 | G | A | Val291Met | 0.017 |
| I9(96) | Intron 9 | C | T | | 0.006 |
| 1295 | Exon 10 | G | A | Arg432Lys | 0.006 |
| 1991 | 3′-UTR | T | A | | 0.289 |

*Subscripts represent the number of times that the indicated trinucleotide is repeated

Example 3

Linkage Disequilibrium Analysis

Linkage disequilibrium analysis was performed for all possible pairwise combinations of PAPSS2 polymorphisms. The EH program developed by Terwilliger and Ott, supra, was used to calculate D′ values, which reflect the degree of linkage between two loci. D′ values can range from +1.0 when two polymorphisms are maximally positively associated to −1.0 when two polymorphisms never occur together (Hartl and Clark, supra; and Hedrick, supra). Since the majority of the PAPSS2 polymorphisms had frequencies of less than 2.5%, there was inadequate statistical power to perform linkage analysis for most of them. However, the analysis did show a highly positive linkage between two common polymorphisms, the G→A transition at nucleotide 17 in intron 7 (frequency 9.4%) and the T→A transversion at nucleotide 1991 in the 3′-UTR (frequency 28.9%; D′=0.80, P<0.001).

Example 4

Activity of Variant PAPSS2 Polypeptides

Cell homogenate preparations containing recombinant PAPSS2 allozymes, prepared as described in Example 1, were used to assess catalytic activity. Expression constructs were created for each of the 4 nonsynonymous PAPSS2 cSNPs were used to transiently transfect COS-1 cells. After transfection, the COS-1 cell preparations were assayed for PAPSS activity under optimal conditions for the wild type enzyme (Xu et al., 2001, supra). The resulting activities were adjusted to a percentage of the wild type PAPSS2 enzyme activity.

The loxP-modified p91023(b) expression system proved to be superior to commercially available vectors such as pcDNA4 and pCR3.1 (Venkatachalam et al., *J. Biol. Chem.*, 273:19311–19320 (1998)) with regard to levels of expression obtained. Specifically, when compared with basal levels of endogenous PAPSS activity in COS-1 cells, overexpression of wild type PAPSS2 using the loxP-modified p91023 (b) vector produced a greater than 7-fold increase in activity. However, only a 2-fold increase could be achieved when pcDNA4 was used as the acceptor vector.

Two of the four recombinant allozymes displayed significant decreases in PAPSS activity as compared to the wild type sequence after correction for transfection efficiency (Table 3). Expression of the common Val291Met polymorphism resulted in a 62.9% decrease in enzyme activity (P<0.0001), while the Glu10Lys allozyme showed a smaller—but still significant—decrease in enzyme activity of 27.4% (P<0.01) when compared with the wild type enzyme. Both Arg432Lys and Met281Leu exhibited activities greater than the wild type enzyme (104.8% and 107.7%, respectively). To assure that the His-tag on the recombinant allozyme proteins had not affected these results, the wild type, Glu10Lys and Val291Met inserts also were expressed in the non-His-tagged expression vector p91023(b). The results of those experiments, corrected for transfection efficiency, were very similar to those obtained with His-tagged recombinant proteins. Specifically, activity of the Val291Met allozyme was reduced 57.4% (P<0.0001), while that of the Glu10Lys allozyme was reduced 14.1% (P<0.05).

TABLE 3

Recombinant human PAPSS2 biochemical properties

| Polymorphism | Amino Acid Change | % WT activity |
|---|---|---|
| G28A | Glu10Lys | 72.6 ± 7.2 |
| A841T | Met281Leu | 107.7 ± 2.9 |
| G871A | Val291Met | 37.1 ± 6.9 |
| G1295A | Arg432Lys | 104.8 ± 10.1 |
| wild type | none | 100 |

Example 5

Western Blot Analysis

To determine whether decreases in levels of variant allozyme PAPSS2 activity might be related to quantity of immunoreactive enzyme protein, quantitative Western blot analyses were conducted. The decrease in enzyme activity for the Glu10Lys allozyme was paralleled by a significant reduction in the level of immunoreactive protein. Furthermore, these COS-1 cell preparations contained β-galactosidase activity similar to that observed with other recombinant allozymes. The enzyme activity results thus were not the result of low transfection efficiency. Although expression of the Val291 Met variant allozyme also was associated with a significantly decreased level of enzyme activity, expression of this construct did not result in a change in the level of immunoreactive protein.

Example 6

Substrate Kinetic Studies

Alterations in amino acid sequence can alter enzyme substrate affinity and/or catalytic efficiency. Decreased activity of the Val291Met allozyme—without a significant alteration in level of enzyme protein—could have resulted from a change in substrate kinetics. Therefore, a series of ATP (0.125–4 mM) and $Na_2SO_4$ (0.125–16 mM) concentrations were used to estimate apparent $K_m$ values for recombinant wild type PAPSS2 and for the Val291Met variant allozyme. In the course of performing those experiments, it became clear that PAPSS2 kinetics for ATP for both wild type and the Val291Met variant exhibited allosteric characteristics that were best described by the Hill equation (FIG. 5A). ATP concentrations at which 50% maximal velocity was achieved ($S_{50}$ values) were 0.70 and 0.95 mM for the wild type and variant allozymes, respectively (Table 4). In both cases, the Hill coefficient was greater than 2, indicating substrate inhibition. In contrast, substrate kinetics of both allozymes for $Na_2SO_4$ conformed to Michaelis-Menten predictions (FIG. 5B). The Val291Met allozyme, however, had a significantly higher $K_m$ value for $Na_2SO_4$ (3.0 mM) than did the wild type enzyme (0.87 mM) ($P<0.001$). Therefore, the ratios of "relative $V_{max}$" for the variant allozyme over apparent $K_m$ values for $Na_2SO_4$ or $S_{50}$ values for ATP were significantly lower than were those for wild type protein (Table 4). In summary, decreased activity for the Val1291Met variant appeared to result from an alteration in substrate kinetics, while decreased activity for the Glu10Lys allozyme, in contrast, resulted primarily from a decrease in the quantity of enzyme protein. Because the Val291Met variant was encoded by a construct that contained the most common PAPSS2 nonsynonymous cSNP, these observations could have functional implications for the sulfate conjugation of both endogenous and/or exogenous compounds.

TABLE 4

Substrate kinetics for wild type and Val291Met PAPSS2

| Substrate | Kinetic Parameter | Wild Type | Val291Met |
|---|---|---|---|
| ATP | Kinetic model | Allosteric | Allosteric |
| | $S_{50}$ (mM) | 0.70 ± 0.01 | 0.95 ± 0.02* |
| | Hill coefficient | 5.4 ± 0.1 | 4.1 ± 0.10 |
| | $V_{max}$ | 100 | 37 ± 3.9* |
| | $V_{max}/S_{50}$ | 100 | 27.8 ± 3.3* |
| $Na_2SO_4$ | Kinetic model | Michaelis-Menten | Michaelis-Menten |
| | $K_m$ (mM) | 0.87 ± 0.01 | 3.0 ± 0.14* |
| | $V_{max}$ | 100 | 45 ± 2.4* |
| | $V_{max}/K_m$ | 100 | 13.6 ± 1.3* |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting essentially of a variant PAPSS2 nucleic acid sequence, wherein said variant PAPSS2 nucleic acid sequence is selected from the group consisting of:
  a) at least 15 contiguous nucleotides of SEQ ID NO:1, wherein said sequence includes one or both of nucleotide positions 359 and 828 of SEQ ID NO:1, with the proviso that the nucleotide at position 359 of SEQ ID NO:1 is cytosine or the nucleotide at position 828 of SEQ ID NO:1 is adenine, or wherein said sequence encompasses a deletion of the nucleotides at positions 387 to 467 of SEQ ID NO:1, a deletion of one or two GCT repeats at positions 758 to 781 of SEQ ID NO:1, or an insertion of one, two, three, or four GCT repeats between positions 758 and 781 of SEQ ID NO:1;
b) at least 15 contiguous nucleotides of SEQ ID NO:8, wherein said sequence includes one or more of nucleotide positions 108, 356, 692, 921, 951, or 1375 of SEQ ID NO:8, with the proviso that the nucleotide at position 108 of SEQ ID NO:8 is adenine, the nucleotide at position 356 of SEQ ID NO:8 is cytosine, the nucleotide at position 692 of SEQ ID NO:8 is thymine, the nucleotide at position 921 of SEQ ID NO:8 is thymine, the nucleotide at position 951 of SEQ ID NO:8 is adenine, or the nucleotide at position 1375 of SEQ ID NO:8 is adenine;
c) at least 15 contiguous nucleotides of SEQ ID NO:2, wherein said sequence includes nucleotide position 64 of SEQ ID NO:2, with the proviso that the nucleotide at position 64 of SEQ ID NO:2 is thymine, or wherein said sequence encompasses a deletion of the nucleotides at positions 130 to 133 of SEQ ID NO:2;
d) at least 15 contiguous nucleotides of SEQ ID NO:2, wherein said sequence includes nucleotide position 319 of SEQ ID NO:2, with the proviso that the nucleotide at position 319 of SEQ ID NO:2 is adenine, or wherein said sequence encompasses one or two AT insertions between position 299 and 312 of SEQ ID NO:2, or;
e) at least 15 contiguous nucleotides of SEQ ID NO:3, wherein said sequence includes nucleotide 1106 of SEQ ID NO:3, with the proviso that the nucleotide at position 1106 of SEQ ID NO:3 is adenine;
f) at least 15 contiguous nucleotides of SEQ ID NO:3, wherein said sequence includes nucleotide 1306 of SEQ ID NO:3, with the proviso that the nucleotide at position 1306 of SEQ ID NO:3 is adenine;
g) at least 15 contiguous nucleotides of SEQ ID NO:3, wherein said sequence includes one or both of nucleotide positions 1699 and 1820 of SEQ ID NO:3, with the proviso that the nucleotide at position 1699 of SEQ ID NO:3 is adenine or the nucleotide at position 1820 of SEQ ID NO:3 is thymine;
h) at least 15 contiguous nucleotides of SEQ ID NO:3, wherein said sequence includes nucleotide 2205 of SEQ ID NO:3, with the proviso that the nucleotide at position 2205 of SEQ ID NO:3 is cytosine;
i) at least 15 contiguous nucleotides of SEQ ID NO:4, wherein said sequence includes one or more of nucleotide positions 86, 115, or 151 of SEQ ID NO:4, with the proviso that the nucleotide at position 86 of SEQ ID NO:4 is guanine, the nucleotide at position 115 of SEQ ID NO:4 is guanine, or the nucleotide at position 151 of SEQ ID NO:4 is guanine;
j) at least 15 contiguous nucleotides of SEQ ID NO:5, wherein said sequence includes nucleotide 425 of SEQ ID NO:5, with the proviso that the nucleotide at position 425 of SEQ ID NO:5 is thymine; and
k) the complement of a), b), c), d), e), f), g), h), i), or j).

2. The isolated nucleic acid molecule of claim 1, wherein said PAPSS2 nucleic acid sequence is at least 15 contiguous nucleotides of SEQ ID NO:8, wherein said sequence includes one or more of nucleotide positions 108, 921, 951, or 1375 of SEQ ID NO:8, with the proviso that the nucleotide at position 108 of SEQ ID NO:8 is adenine, the nucleotide at position 921 of SEQ ID NO:8 is thymine, the nucleotide at position 951 of SEQ ID NO:8 is adenine, or the nucleotide at position 1375 of SEQ ID NO:8 is adenine.

3. The isolated nucleic acid molecule of claim 1, wherein said PAPSS2 nucleic acid sequence is at least 15 contiguous nucleotides of SEQ ID NO:8, wherein said sequence includes one or both of nucleotide positions 356 and 692 of SEQ ID NO:8, with the proviso that the nucleotide at position 356 of SEQ ID NO:8 is cytosine or the nucleotide at position 692 of SEQ ID NO:8 is thymine.

4. The isolated nucleic acid molecule of claim 1, wherein said PAPSS2 nucleic acid sequence is at least 15 contiguous nucleotides of SEQ ID NO:2, wherein said sequence includes nucleotide position 64 of SEQ ID NO:2, with the proviso that the nucleotide at position 64 of SEQ ID NO:2 is thymine, or wherein said sequence encompasses a deletion of the nucleotides at positions 130 to 133 of SEQ ID NO:2.

5. The isolated nucleic acid molecule of claim 1, wherein said PAPPS2 nucleic acid sequence is at least 15 contiguous nucleotides of SEQ ID NO:2, wherein said sequence includes nucleotide position 319 of SEQ ID NO:2, with the proviso that the nucleotide at position 319 of SEQ ID NO:2 is adenine, or wherein said sequence encompasses one or two AT insertions between position 299 and 312 of SEQ ID NO:2.

6. The isolated nucleic acid molecule of claim 1, wherein said PAPPS2 nucleic acid sequence is at least 15 contiguous nucleotides of SEQ ID NO:3, wherein said sequence includes nucleotide 1106 of SEQ ID NO:3, with the proviso that the nucleotide at position 1106 of SEQ ID NO:3 is adenine.

7. The isolated nucleic acid molecule of claim 1, wherein said PAPPS2 nucleic acid sequence is at least 15 contiguous nucleotides of SEQ ID NO:3, wherein said sequence includes nucleotide 1306 of SEQ ID NO:3, with the proviso that the nucleotide at position 1306 of SEQ ID NO:3 is adenine.

8. The isolated nucleic acid molecule of claim 1, wherein said PAPPS2 nucleic acid sequence is at least 15 contiguous nucleotides of SEQ ID NO:3, wherein said sequence includes one or both of nucleotide positions 1699 and 1820 of SEQ ID NO:3, with the proviso that the nucleotide at position 1699 of SEQ ID NO:3 is adenine or the nucleotide at position 1820 of SEQ ID NO:3 is thymine.

9. The isolated nucleic acid molecule of claim 1, wherein said PAPPS2 nucleic acid sequence is at least 15 contiguous nucleotides of SEQ ID NO:3, wherein said sequence includes nucleotide 2205 of SEQ ID NO:3, with the proviso that the nucleotide at position 2205 of SEQ ID NO:3 is cytosine.

10. The isolated nucleic acid molecule of claim 1, wherein said PAPPS2 nucleic acid sequence is at least 15 contiguous nucleotides of SEQ ID NO:4, wherein said sequence includes one or more of nucleotide positions 86, 115, or 151 of SEQ ID NO:4, with the proviso that the nucleotide at position 86 of SEQ ID) NO:4 is guanine, the nucleotide at position 115 of SEQ ID NO:4 is guanine, or the nucleotide at position 151 of SEQ ID NO:4 is guanine.

11. The isolated nucleic acid molecule of claim 1, wherein said PAPPS2 nucleic acid sequence is at least 15 contiguous nucleotides of SEQ ID NO:5, wherein said sequence includes nucleotide 425 of SEQ ID NO:5, with the proviso that the nucleotide at position 425 of SEQ ID NO:5 is thymine.

12. The isolated nucleic acid molecule of claim 1, wherein said PAPPS2 nucleic acid sequence is at least 15 contiguous nucleotides of SEQ ID NO: 1, wherein said sequence includes one or both of nucleotide positions 359 and 828 of SEQ ID NO:1, with the proviso that the nucleotide at position 359 of SEQ ID NO: 1 is cytosine or the nucleotide at position 828 of SEQ ID NO: 1 is adenine, or wherein said sequence encompasses a deletion of the nucleotides at positions 387 to 467 of SEQ ID NO: 1, a deletion of one or two GCT repeats from position 758 to 781 of SEQ ID NO:1, or an insertion of one, two, three, or four GCT repeats between positions 758 and 781 of SEQ ID NO: 1.

13. An isolated nucleic acid encoding a PAPSS2 polypeptide, wherein said polypeptide has the amino acid sequence of SEQ ID NO:9, with the proviso that the amino acid residue at one or more of positions 10, 281, 291, and 432 is a variant amino acid.

14. The isolated nucleic acid of claim 13, wherein said variant amino acid is selected from the group consisting of a lysine at residue 10, a leucine at residue 281, a methionine at residue 291, and a lysine at residue 432.

15. The isolated nucleic acid of molecule of claim 1, wherein said isolated nucleic acid molecule is from 15 to 100 nucleotides in length.

16. The isolated nucleic acid of molecule of claim 1, wherein said isolated nucleic acid molecule is from 20 to 50 nucleotides in length.

17. A vector comprising the nucleic acid molecule of claim 1.

18. The vector of claim 17, wherein said nucleic acid molecule is from 20 to 50 nucleotides in length.

* * * * *

UNITED STATES PATENT AND TRADEMARK OFFICE
CERTIFICATE OF CORRECTION

PATENT NO. : 7,186,551 B1  Page 1 of 1
APPLICATION NO. : 10/294397
DATED : March 6, 2007
INVENTOR(S) : Zhenhua Xu, Eric D. Wieben and Richard M. Weinshilboum It is certified that error appears in the above-identified patent and that said Letters Patent is hereby corrected as shown below:

Title Page, References Cited, Item [56], Other Publications, K. Kurima et al. reference, please delete "Activiating" and insert --Activating-- therefor;

Title Page, References Cited, Item [56], Other Publications, Z. Xu et al. reference, please delete "Hu7man" and insert --Human-- therefor;

Column 57, line 66, claim 3, please delete "PAPPS2" and insert --PAPSS2-- therefor;

Column 58, line 14, claim 5, please delete "PAPPS2" and insert --PAPSS2-- therefor;

Column 58, line 22, claim 6, please delete "PAPPS2" and insert --PAPSS2-- therefor;

Column 58, line 28, claim 7, please delete "PAPPS2" and insert --PAPSS2-- therefor;

Column 58, line 34, claim 8, please delete "PAPPS2" and insert --PAPSS2-- therefor;

Column 58, line 41, claim 9, please delete "PAPPS2" and insert --PAPSS2-- therefor;

Column 58, line 47, claim 10, please delete "PAPPS2" and insert --PAPSS2-- therefor;

Column 58, line 55, claim 11, please delete "PAPPS2" and insert --PAPSS2-- therefor;

Column 58, line 61, claim 12, please delete "PAPPS2" and insert --PAPSS2-- therefor.

Signed and Sealed this

Thirty-first Day of July, 2007

JON W. DUDAS
*Director of the United States Patent and Trademark Office*

SEQUENCE LISTING

<160> NUMBER OF SEQ ID NOS: 41

<210> SEQ ID NO 1
<211> LENGTH: 1084
<212> TYPE: DNA
<213> ORGANISM: Homo sapiens

<400> SEQUENCE: 1

```
tggaagcccc tcagcacgat gcatagtgaa cagacaagct gtgaaccttg ggagttatca      60
ccatgtgtga tgatgctggt gaagaaagcc tgcactgagg aggctgtcag cctgggtttg     120
aatcccctca tttggaatat aatcttggca aagtctgaaa gcctcaattg ctcgtttgta     180
aaactggaag atagtaggac ttgctgcccg gggtcggggc aggatggagg gggcccatga     240
gaattaaggc agagcccagc ggagtgcatt gtaaggatcc atgagtgtga accttcgttt     300
ttactactgc atatgaggat cctgccaaca aacctggcgg cttcaagcat ccttgccctt     360
aaccaaataa gctcttaggt cctagaggca ggaagacttc cttgaagagg cgcgggaggc     420
tggtgagggg agtggaggac gctctgggac cctctggggg tggggcgggc ggggtgaact     480 tgacccagg ccgcgtgccg ggcgtgccat ctgccgctcc gctgcaaggt ctcgcccggg     540
accggggctg gcggagcgcg cgcccgcgag taggggccgg gccgggacc ccgcctagc      600 ggcggcggcc gggtccccaa ggctgggcgc tgcttgcgga accgacgggg cggagaggag     660
cgtggcggga ggaggagtag gagaaggggg ctggtcaagg gaagtgcgac gtgtctgcgg     720
agccttttta tacctccttc ccgggagtcc ggcagccgct gctgctgctg ctgctgctgc     780
```

-continued

```
tgccgccgcc gccgccgccg tccctgcgtc cttcggtctc tgctcccggg acccgggctc    840
cgccgcagcc agccagcatg tcggggatca agaagcaaaa gacggtaggc ttccaggcgc    900
cggcttccct ccccgccacc gcactgcacg cgccgacccc caacccccaa ttccccggca    960
cttgggtccc accctccccg ggaggggcg tcgggaggag gagtaagagt ggggcacgga   1020
gggaagcaag agaaagaggc tctgtgtgga attcccgggg cagtcctcgc cccgcagccc   1080
ctct                                                                1084

<210> SEQ ID NO 2
<211> LENGTH: 484
<212> TYPE: DNA
<213> ORGANISM: Homo sapiens

<400> SEQUENCE: 2
ctatattaga atggacaaag gtgagtctct ttcaaaatat ttttatata agttgttaca      60 tgtatcagtt tcgcaattaa aagtttaaga tggatttata ttggctccag tgaagaatat   120
gtgttttatt aattaatact gtgcttggtt ttgtcttatt ttataggaga accagcagaa   180
atccaccaat gtagtctatc aggcccacca tgtgagcagg aataagagag ggcaagtggt   240
tggaacaagg ggtgggttcc gaggatgtac cgtgtggcta acaggtatgt catgttcata   300
tatatatata tacaaattgc aaactgacat gtgacacaat tttatggaaa ttagtgtaac   360
gtattacatg cttgttttat cattagaagg aggctgggag atgtagtaga aagcctgggt   420
gttagtccta accctaccat cagtgagaaa tagagtcaag gtcaactaca gaaataagag   480
tctg                                                                484

<210> SEQ ID NO 3
<211> LENGTH: 3146
<212> TYPE: DNA
<213> ORGANISM: Homo sapiens

<400> SEQUENCE: 3
taagtacttg ccttgtagtc aactacactg atttctttct ttctttttt tttttttaag     60 atttagttat atttaaaatt actagattag ttcacaattt gtcatcttaa actatccagg   120
ccgatgtcag tctgttttat ctgttctgaa caggtctctc tggtgctgga aaaacaacga   180
taagttttgc cctggaggag taccttgtct cccatgccat cccttgttac tccctggatg   240
gggacaatgt ccgtcatggc cttaacagaa atctcggatt ctctcctggg gacagagagg   300
aaaatatccg ccggattgct gaggtggcta agctgtttgc tgatgctggt ctggtctgca   360
ttaccagctt tatttctcca ttcgcaaagg taaaaaaaa aaaaaaaaa aaaaaaaaaa     420 aaaaaaaaa aaaaaaggc actacacacg attcccacac acagtgcaag tgctctccaa     480
ctgctagggg aaggaatcgg agagggaggg cataagaatg tctcctttca atttcccgac    540
tatttcttcc cccaataaca ggctctctca tttcctctat ttaatattgg ttatataaag    600
gagttccttc ctttccagat gccagggcac cagtagacat aaaccctcc atgttcacaa    660 ttataaggaa catttggtga gagtcgaagg gaagagaaag ttaaacaaga gaaactctaa    720
acctctgtaa tttagttgt cggaaaaagg atctagttaa agaaagagc agttcatggc     780 caaagcttcg ggttctatgt gtttaatgct gacatcactg aggtggagtg tcactcttct    840
tttaaatcag gaaatttctg ggagccaaac atcagatgta gcttagaaca catccttga    900 atgaaatgct cccatatggc cagtgctttc ctgctaagag ggcctatttt ccatgatttt    960
```

-continued

```
ctgtgaaagt ccttgagaga gctgtgttta ccagagtaaa atttctggac tttctctcaa    1020
gcactctgca aagcacaaac cccagtgtta tctcaaggct attgaaaacc aaagtacaca    1080
gtgttttgtg atttagaatt tcaccgtgaa acctcttttt acattcttaa tcatattgct    1140
tttcaggatc gtgagaatgc ccgcaaaata catgaatcag cagggctgcc attctttgaa    1200
atatttgtag atgcacctct aaatatttgt gaaagcagag acgtaaaagg cctctataaa    1260
agggccagag ctggggagat taaggtaag agaattggct agtagcgtct accagttaca     1320
taggctgtca gtcctcagtc cttattctgt cctcagaaat cttccttgag tttcaaactg    1380
ttttccaaaa ttgcatataa catgcacaac ttttttattag atcatgatat attcagtatg   1440
cccagaggct tattaaaagg tagggttttta tttttaagaa ttgtcatctc agccatatgc   1500
aataacgttc agagaactag aatggatatt tatatgtgag tgtgtgtgtg tagaggagtg    1560
tttcagagtt cttccttatt cttgtcttcc tttttgattg taatcatcta tagagggctt    1620
caacttagcc agcgggattt tgttgacaat ttggggcttt ccatattgaa aatacagcta    1680
tatattttct tacttatggc tagaagtcaa ggatggctgt ttgaccttt ctgttaaagt     1740 gtgaattttc agtttaatac attattccaa catgtgttttt gccttattga ttaaaaagat   1800
tattctgtca atacagatgc gatgattgtc acccatatgc tttgcaggat ttacaggtat    1860
tgattctgat tatgagaaac ctgaaactcc tgagcgtgtg cttaaaacca atttgtccac    1920
agtgagtgac tgtgtccacc aggtagtgga acttctgcaa gagcaggtag gtgaaccggt    1980 tgtcttttttt tatatgttta ataaaatcat gaaagacaat ctatgcctct ttactgaagc   2040 attctttttta cagtttttcaa gttttttacca atgctgtttc atttcagaac attgtaccct  2100
atactataat caaagatatc cacgaactct ttgtgccgga aaacaaactt gaccacgtcc    2160
gagctgaggc tgaaactctc ccttcattat caattactaa ggtaagtggg tgcagactgg    2220
tcaaataatt aggcttaata tcagtcatta taatttattt acaattactc ttaacaataa    2280
gaaaagtata ataaggtgc acataatgtc cataaataaa acactccttt ttttccaagt     2340
tatttttaac ctcttctcca agaaatctc tcaccaagaa ttgccacaag gcagctgatc     2400
aatgccatgt atggaggtga ctgggaaaat aacttctgta tttgcattgg acaatttac     2460 atagctgtca ttgtaccagt aagtacatct ggtagaaaaa tatagccaga ccaggatttt    2520
tgtggataaa agaaagaaag aataaacagt gaattttcaa ctcagttgca cattttggga   2580
atagatacaa cctaaaaatg ttcaaataag tcatctcaat acaaaatctt ttcaccacta   2640
tttcatagga aacttccaaa cttaaatatt tctggcccctt agatcatggg ttagcataac   2700
aggtggggac acttaaaaca tagaaggttc tgccctcatc ctcctgttaa ctgaataaga   2760
aaggacttcc ctggggccag atgcctggaa aacagaactt atgaaaatgt tcaactactt   2820 tttgtgttttt gcagctggat ctccagtggg tccaggtttt gagcgaaggc tgggccactc   2880
ccctcaaagg tttcatgcgg gagaaggagt acttacaggt tatgcacttt gacaccctgc    2940
tagatggtat gtttttgttg ttgtttctta ctctttgttg ttaaggaaaa aaaaaatctt    3000
tcccagaagt tttgcaggaa caggaagtta gtctttggtt tgcaaatctt attgcaaaac    3060
tatttggatc atttacagtg tgctccattc tattatgttt aagcttccat ttttaggatt    3120
ttttggttgt tctcaaaggt tgttcc                                         3146
```

<210> SEQ ID NO 4
<211> LENGTH: 590
<212> TYPE: DNA
<213> ORGANISM: Homo sapiens

<400> SEQUENCE: 4

```
cccttcaagg acttgtcatt atagaatcta gagaaactgg tgcagctaac acaactactt    60
ggatttgggt cttaatgctt cttgaaggaa atgtttggaa gggcattgt gcacatttga    120
ttcatgcttc aaggatggca caccttatat ctagttttcg tgcatcacat ggctctttcc   180
acagatggcg tgatcaacat gagcatcccc attgtactgc ccgtctctgc agaggataag   240
acacggctgg aagggtgcag caagtttgtc ctggcacatg gtggacggag ggtagctatc   300
ttacgagacg ctgaattcta tgaacacaga aagaggaac gctgttcccg tgtttggggg    360
acaacatgta caaaacaccc ccatatcaaa gtaagtcaca aaacctttgg aaggactttc   420
ttgagctatt taaactgaga agaaaaataa ctcttttttaa ttcctttgca aaggacttag  480
aaaaactggg attaggtgga agaatgtatt tctaaggtag tgtttgcagg ctttgcctca   540
ggagatgttt ttagaaaggt gcaaagaaat gtctttctgt ttgaggtctg             590
```

<210> SEQ ID NO 5
<211> LENGTH: 529
<212> TYPE: DNA
<213> ORGANISM: Homo sapiens

<400> SEQUENCE: 5

```
ggtactcaat aattttttaa gagcataacg ggttctagag accaaaaagt ttgagaaata   60
ctgtgccaga atactaaag aactgaaggc agttctttaa ctgtaacccg agattggtct    120
aaaaggagaa aacttttcag ataaaataga atcacaatt aatcattagc aatcataaca    180
atgttctttc tagatggtga tggaaagtgg ggactggctg ttggtggag accttcaggt    240
gctggagaaa ataagatgga atgatgggct ggaccaaatac cgtctgacac ctctggagct   300
caaacagaaa tgtaaagaaa tgaatgctgg tatgtaaact gttcttagtg cattttattt   360
atttatttat tgagatggtg tcttgttctg tcacccaggc tggagtgcaa tggcacgatc   420
tcagctcact gcaacctctg cctcccaggt tcaagtaatt ctcctgcctc agcctcctga   480
gtagcttgga ttacaggtgc ccaccaccac gcccagctaa ttttttgtat             529
```

<210> SEQ ID NO 6
<211> LENGTH: 665
<212> TYPE: DNA
<213> ORGANISM: Homo sapiens

<400> SEQUENCE: 6

```
aggcggaggt tgcagtgacc tgagatcgct gactgcactc cagcctgggc aacagagtga   60
gactctttca aaaaaaaaaa aagccagtgg ataatgaatg cacagaacaa taaacatagc   120
tgtgtccttt ctgttcttgt ggagaaatga caccatgtgt ttctgtgacc ttccttcttc   180
tgctttcctc tcccagatgc ggtgtttgca ttccagttgc gcaatcctgt ccacaatggc   240
catgccctgt tgatgcagga cacctgccgc aggctcctag agaggggcta caagcacccg   300
gtcctcctac tacaccctct gggcggctgg accaaggatg acgatgtgcc tctagactgg   360
cggatgaagc agcacgcggc tgtgctcgag aagggggtcc tggatcccaa gtcaaccatt   420
gttgccatct ttccgtctcc catgttatat gctggcccca cagaggtgag caattcccag   480
agctgggctt tgagactcag gaattcagac tcagacttta catagaagag taaatgagtc   540
tctgggatcc tttctgtttc ctcatgagca gattctggaa tgttctggtg tctcttcttt   600
atctagctta attatgtttc cacttagtat ttgaaaagtg ctagaggcc aggcgcagtg    660
```

-continued gctgt 665

<210> SEQ ID NO 7
<211> LENGTH: 3220
<212> TYPE: DNA
<213> ORGANISM: Homo sapiens

<400> SEQUENCE: 7

| | |
|---|---|
| cctacctaat ataacaaagc atgaagagtg cacggagtct tagaacctca gtgattttct | 60 |
| tgcaattctt agttgactca cattgctgaa ttacttttaa agtagaataa aggtgtctcc | 120 |
| ataaaccatg acctacagat ttgacccaca atgaccagca tgtcccttat ggacattttc | 180 |
| taggtccagt ggcactgcag gtcccggatg attgcgggtg ccaatttcta cattgtgggg | 240 |
| agggaccctg caggaatgcc ccatcctgaa accaagaagg atctgtatga acccactcat | 300 |
| gggggcaagg tcttgagcat ggcccctggc ctcacctctg tggaaatcat tccattccga | 360 |
| gtggctgcct acaacaaagc caaaaaagcc atggacttct atgatccagc aaggtaggtt | 420 |
| ttcagaggaa aattctttta tcaacatctg tataaaagaa atgatgaggc agaatttggg | 480 |
| ccctttgaaa aactctccag tgcattgcca catgctccca gtggactgag tcccttgag | 540 |
| agtcaagacg tggtcttata aattttatgt cccctaaaat tgtactacag tcttctgcat | 600 |
| atagtagatg gtccataaat atttctcttt caacatgcat tcttgagcat gcacagagtg | 660 |
| cctggcacac taagtgaaag gaagcaacat agaaagagat tgcaatgaat atttatggtg | 720 |
| cacttgctcc tcatgctgag ggttcacaga agtaggcaga gaaacagaag acagactctg | 780 |
| ggctcaagac acttcccagg aacagtatag gcgcatggca aatactaaat ggatagctgc | 840 |
| cattatttcc cttctcttct gcaagttcct gaagatttag aggactgccc acttttgaag | 900 |
| atgcagcatt ttacagaaag aacatgggtc tcaaaaacca taacctactc caggaatcct | 960 |
| taaggcagat atcatttacc tacactgagt tctttgttgc caccctgtaa caggcacaat | 1020 |
| gagtttgact tcatctcagg aactcgaatg aggaagctcg cccgggaagg agagaatccc | 1080 |
| ccagatggct tcatggcccc caaagcatgg aaggtcctga cagattatta caggtccctg | 1140 |
| gagaagaact aagcctttgg gtccagagtt tctttctgaa gtgctctttg attacctttt | 1200 |
| ctatttttat gattagatgc tttgtattaa attgcttctc aatgatgcat tttaatcttt | 1260 |
| tataatgaag taaagttgt gtctataatt aaaaaaaata tatatatata tacacacaca | 1320 |
| catatacata caaagtcaaa ctgaagacca atcttagca ggtaaaagca atattcttat | 1380 |
| acatttcata ataaaattag ctctatgtat tttctactgc acctgagcag gcaggtccca | 1440 |
| gatttcttaa ggctttgttt gaccatgtgt ctagttactt gctgaaaagt gaatatattt | 1500 |
| tccagcatgt cttgacaacc tgtactcttc caatgtcatt tatcagttgt aaaatatatc | 1560 |
| agattgtgtc cttcttctgt acaattgaca aaaaaaaatt ttttttctc actctaaaag | 1620 |
| aggtgtggct cacatcaaga ttcttcctga tattttacct catgctgtac aagccttaat | 1680 |
| gtgtaatcat atcttacgtg ttgaagacct gactggagaa acaaaatgtg caataacgtg | 1740 |
| aattttatct tagagatctg tgcagcctag attttacctc atgctgtaca aagccttaat | 1800 |
| gttgtaatca tatcttacgt gttgagacct gactggagaa acaaaatgtg caataacgtg | 1860 |
| aattttatct tagagatctg tgcagcctat tttctgtcac aaaagttata ttgtctaata | 1920 |
| agagaagtct taatggcctc tgtgaataat gtaactcagt tacacggtga ctttttaatag | 1980 |
| catacagtga tttgatgaaa ggacgtcaaa caatgtggcg atgtcgtgga aagttatctt | 2040 |
| tcccgctctt tgctgtggtc attgtgtctt gcagaaagga tggccctgat gcagcagcag | 2100 |

-continued

```
cgccagctgt aataaaaaat aattcacact atcagactag caaggcacta gaactggaaa      2160
agaccacaga aaacaaagaa tccaacccct tcatcttaca ggtgaacaaa ctgtgatgat      2220
gcacatgtat gtgttttgta agctgtgagc accgtaacaa aatgtaaatt tgccattatt      2280
aggaaagtgc tggtggcagt gaagaagcac ccaggccact tgactcccag tctggtgccc      2340
tgtctcaccc agacaacaca ggagctgggt cagattcccc tcagctgctt aacaaagttc      2400
ctcgaacaga aagtgcttac aaagctgcct tctcggatac tgaaaggtcg agttttctga      2460
actgcactga ttttattgca gttgaaaaaa aaaagctat tccaaagatt tcaagctgtt       2520
ctgagacatc ttctgatggc tttacttcct gagaggcaat gtttttactt tatgcataat      2580
tcattgttgc caaggaataa agtgaagaaa cagcaccttt aatatatag gtctctctgg       2640 aagagaccta aattagaaag agaaaactgt gacaattttc atattctcat tcttaaaaaa      2700
cactaatctt aactaacaaa agttcttttg agaataagtt acacacaatg gccacagcag      2760 tttgtctttta atagtatagt gcctatactc atgtaatcgg ttactcacta ctgcctttaa     2820
aaaaaaaaac cagcatattt attgaaaaca tgagacagga ttatagtgcc ttaaccgata      2880
tattttgtga cttaaaaaat acatttaaaa ctgctcttct gctctagtac catgcttagt      2940
gcaaatgatt atttctatgt acaactgatg cttgttctta ttttaataaa tttatcagag      3000
tgaaggctga gttttttctg cctgtaccat tgggtgtggg ttgaccacac aacttaaggg      3060
ctttgtgact ttgtataatt ggagtgagac agcagcaact ctcttgaaca tcataactga      3120
gattatttac ccttattcat gtctttttta ttttttattt ttttaaagac gaagtcttgc      3180
tctgtcaccc aggctggagt gctgtggcac gatctcggct                           3220
```

<210> SEQ ID NO 8
<211> LENGTH: 2014
<212> TYPE: DNA
<213> ORGANISM: Homo sapiens

<400> SEQUENCE: 8

```
ctgctgccgc cgccgccgcc gccgtccctg cgtccttcgg tctctgctcc cgggacccgg        60
ctccgccgca gccagccagc atgtcgggga tcaagaagca aaagacggag aaccagcaga       120
aatccaccaa tgtagtctat caggcccacc atgtgagcag gaataagaga gggcaagtgg       180
ttggaacaag gggtgggttc cgaggatgta ccgtgtggct aacaggtctc tctggtgctg       240
gaaaaacaac gataagtttt gccctggagg agtaccttgt ctcccatgcc atcccttgtt       300
actccctgga tggggacaat gtccgtcatg gccttaacag aaatctcgga ttctctcctg       360
gggacagaga ggaaaatatc cgccggattg ctgaggtggc taagctgttt gctgatgctg       420
gtctggtctg cattaccagc tttatttctc cattcgcaaa ggatcgtgag aatgcccgca       480
aaatacatga atcagcaggg ctgccattct ttgaaatatt tgtagatgca cctctaaata       540
tttgtgaaag cagagacgta aaaggcctct ataaagggc cagagctggg gagattaaag       600
gatttacagg tattgattct gattatgaga aacctgaaac tcctgagcgt gtgcttaaaa       660
ccaatttgtc cacagtgagt gactgtgtcc accaggtagt ggaacttctg caagagcaga       720
acattgtacc ctatactata atcaaagata tccacgaact ctttgtgccg gaaaacaaac       780
ttgaccacgt ccgagctgag gctgaaactc tcccttcatt atcaattact aagctggatc       840
tccagtgggt ccaggttttg agcgaaggct gggccactcc cctcaaaggt ttcatgcggg       900
agaaggagta cttacaggtt atgcactttg acaccctgct agatgatggc gtgatcaaca       960
```

-continued

```
tgagcatccc cattgtactg cccgtctctg cagaggataa gacacggctg aagggtgca   1020 gcaagtttgt cctggcacat ggtggacgga gggtagctat cttacgagac gctgaattct   1080
atgaacacag aaaagaggaa cgctgttccc gtgtttgggg gacaacatgt acaaaacacc   1140
cccatatcaa aatggtgatg gaaagtgggg actggctggt tggtggagac cttcaggtgc   1200
tggagaaaat aagatggaat gatgggctgg accaataccg tctgacacct ctggagctca   1260
aacagaaatg taaagaaatg aatgctgatg cggtgtttgc attccagttg cgcaatcctg   1320
tccacaatgg ccatgccctg ttgatgcagg acacctgccg caggctccta gagaggggct   1380
acaagcaccc ggtcctccta ctacaccctc tgggcggctg gaccaaggat gacgatgtgc   1440
ctctagactg gcggatgaag cagcacgcgg ctgtgctcga ggaagggagtc ctggatccca   1500 agtcaaccat tgttgccatc tttccgtctc ccatgttata tgctggcccc acagaggtcc   1560
agtggcactg caggtcccgg atgattgcgg gtgccaattt ctacattgtg gggagggacc   1620
ctgcaggaat gccccatcct gaaaccaaga aggatctgta tgaacccact catgggggca   1680
aggtcttgag catggcccct ggcctcacct ctgtggaaat cattccattc cgagtggctg   1740
cctacaacaa agccaaaaaa gccatggact tctatgatcc agcaaggcac aatgagtttg   1800
acttcatctc aggaactcga atgaggaagc tcgcccggga aggagagaat cccccagatg   1860
gcttcatggc ccccaaagca tggaaggtcc tgacagatta ttacaggtcc ctggagaaga   1920
actaagcctt tgggtccaga gtttctttct gaagtgctct ttgattacct tttctatttt   1980
tatgattaga tgctttgtat taaattgctt ctca                               2014
```

<210> SEQ ID NO 9
<211> LENGTH: 614
<212> TYPE: PRT
<213> ORGANISM: Homo sapiens

<400> SEQUENCE: 9

```
Met Ser Gly Ile Lys Lys Gln Lys Thr Glu Asn Gln Gln Lys Ser Thr
 1               5                  10                  15

Asn Val Val Tyr Gln Ala His His Val Ser Arg Asn Lys Arg Gly Gln
            20                  25                  30

Val Val Gly Thr Arg Gly Gly Phe Arg Gly Cys Thr Val Trp Leu Thr
        35                  40                  45

Gly Leu Ser Gly Ala Gly Lys Thr Thr Ile Ser Phe Ala Leu Glu Glu
    50                  55                  60

Tyr Leu Val Ser His Ala Ile Pro Cys Tyr Ser Leu Asp Gly Asp Asn
65                  70                  75                  80

Val Arg His Gly Leu Asn Arg Asn Leu Gly Phe Ser Pro Gly Asp Arg
                85                  90                  95

Glu Glu Asn Ile Arg Arg Ile Ala Glu Val Ala Lys Leu Phe Ala Asp
            100                 105                 110

Ala Gly Leu Val Cys Ile Thr Ser Phe Ile Ser Pro Phe Ala Lys Asp
        115                 120                 125

Arg Glu Asn Ala Arg Lys Ile His Glu Ser Ala Gly Leu Pro Phe Phe
    130                 135                 140

Glu Ile Phe Val Asp Ala Pro Leu Asn Ile Cys Glu Ser Arg Asp Val
145                 150                 155                 160

Lys Gly Leu Tyr Lys Arg Ala Arg Ala Gly Glu Ile Lys Gly Phe Thr
                165                 170                 175

Gly Ile Asp Ser Asp Tyr Glu Lys Pro Glu Thr Pro Glu Arg Val Leu
            180                 185                 190
```

-continued

```
Lys Thr Asn Leu Ser Thr Val Ser Asp Cys Val His Gln Val Val Glu
            195                 200                 205
Leu Leu Gln Glu Gln Asn Ile Val Pro Tyr Thr Ile Ile Lys Asp Ile
        210                 215                 220
His Glu Leu Phe Val Pro Glu Asn Lys Leu Asp His Val Arg Ala Glu
225                 230                 235                 240
Ala Glu Thr Leu Pro Ser Leu Ser Ile Thr Lys Leu Asp Leu Gln Trp
                245                 250                 255
Val Gln Val Leu Ser Glu Gly Trp Ala Thr Pro Leu Lys Gly Phe Met
            260                 265                 270
Arg Glu Lys Glu Tyr Leu Gln Val Met His Phe Asp Thr Leu Leu Asp
        275                 280                 285
Asp Gly Val Ile Asn Met Ser Ile Pro Ile Val Leu Pro Val Ser Ala
    290                 295                 300
Glu Asp Lys Thr Arg Leu Glu Gly Cys Ser Lys Phe Val Leu Ala His
305                 310                 315                 320
Gly Gly Arg Arg Val Ala Ile Leu Arg Asp Ala Glu Phe Tyr Glu His
                325                 330                 335
Arg Lys Glu Glu Arg Cys Ser Arg Val Trp Gly Thr Thr Cys Thr Lys
            340                 345                 350
His Pro His Ile Lys Met Val Met Glu Ser Gly Asp Trp Leu Val Gly
        355                 360                 365
Gly Asp Leu Gln Val Leu Glu Lys Ile Arg Trp Asn Asp Gly Leu Asp
    370                 375                 380
Gln Tyr Arg Leu Thr Pro Leu Glu Leu Lys Gln Lys Cys Lys Glu Met
385                 390                 395                 400
Asn Ala Asp Ala Val Phe Ala Phe Gln Leu Arg Asn Pro Val His Asn
                405                 410                 415
Gly His Ala Leu Leu Met Gln Asp Thr Cys Arg Arg Leu Leu Glu Arg
            420                 425                 430
Gly Tyr Lys His Pro Val Leu Leu His Pro Leu Gly Gly Trp Thr
        435                 440                 445
Lys Asp Asp Asp Val Pro Leu Asp Trp Arg Met Lys Gln His Ala Ala
    450                 455                 460
Val Leu Glu Glu Gly Val Leu Asp Pro Lys Ser Thr Ile Val Ala Ile
465                 470                 475                 480
Phe Pro Ser Pro Met Leu Tyr Ala Gly Pro Thr Glu Val Gln Trp His
                485                 490                 495
Cys Arg Ser Arg Met Ile Ala Gly Ala Asn Phe Tyr Ile Val Gly Arg
            500                 505                 510
Asp Pro Ala Gly Met Pro His Pro Glu Thr Lys Lys Asp Leu Tyr Glu
        515                 520                 525
Pro Thr His Gly Gly Lys Val Leu Ser Met Ala Pro Gly Leu Thr Ser
    530                 535                 540
Val Glu Ile Ile Pro Phe Arg Val Ala Ala Tyr Asn Lys Ala Lys Lys
545                 550                 555                 560
Ala Met Asp Phe Tyr Asp Pro Ala Arg His Asn Glu Phe Asp Phe Ile
                565                 570                 575
Ser Gly Thr Arg Met Arg Lys Leu Ala Arg Glu Gly Glu Asn Pro Pro
            580                 585                 590
Asp Gly Phe Met Ala Pro Lys Ala Trp Lys Val Leu Thr Asp Tyr Tyr
        595                 600                 605
```

Arg Ser Leu Glu Lys Asn
      610

<210> SEQ ID NO 10
<211> LENGTH: 81
<212> TYPE: DNA
<213> ORGANISM: Homo sapiens

<400> SEQUENCE: 10
ggcaggaaga cttccttgaa gaggcgcggg aggctggtga ggggagtgga ggacgctctg     60
ggaccctctg ggggtggggc g                                              81

<210> SEQ ID NO 11
<211> LENGTH: 12
<212> TYPE: DNA
<213> ORGANISM: Homo sapiens

<400> SEQUENCE: 11
gctgctgctg ct                                                         12

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
tgtaaaacga cggccagt                                                   18

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
caggaaacag ctatgacc                                                   18

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
atgtcgggga tcaagaagca aaagacg                                         27

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggcttagttc ttctccaggg acct                                            24

<210> SEQ ID NO 16
<211> LENGTH: 42
<212> TYPE: DNA
<213> ORGANISM: Artificial Sequence
<220> FEATURE:

<223> OTHER INFORMATION: Primer

<400> SEQUENCE: 16
tgtaaaacga cggccagtga gcccagcgga gtgcattgta ag                42

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
caggaaacag ctatgaccag gtataaaaag gctccgcaga cacg              44

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
tgtaaaacga cggccagtgc tggtcaaggg aagtgcgacg                   40

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
caggaaacag ctatgaccgt gccccactct tactcctcct c                 41

<210> SEQ ID NO 20
<211> LENGTH: 53
<212> TYPE: DNA
<213> ORGANISM: Artificial Sequence
<220> FEATURE:
<223> OTHER INFORMATION: Primer

<400> SEQUENCE: 20
tgtaaaacga cggccagtct atattagaat ggacaaaggt gagtctcttt caa    53

<210> SEQ ID NO 21
<211> LENGTH: 49
<212> TYPE: DNA
<213> ORGANISM: Artificial Sequence
<220> FEATURE:
<223> OTHER INFORMATION: Primer

<400> SEQUENCE: 21
caggaaacag ctatgaccct atttctcact gatggtaggg ttaggacta         49

<210> SEQ ID NO 22
<211> LENGTH: 56
<212> TYPE: DNA
<213> ORGANISM: Artificial Sequence
<220> FEATURE:
<223> OTHER INFORMATION: Primer

<400> SEQUENCE: 22
tgtaaaacga cggccagtaa gatttagtta tatttaaaat tactagatta gttcac  56

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
caggaaacag ctatgaccgt tggagagcac ttgcactgt                         39

<210> SEQ ID NO 24
<211> LENGTH: 47
<212> TYPE: DNA
<213> ORGANISM: Artificial Sequence
<220> FEATURE:
<223> OTHER INFORMATION: Primer

<400> SEQUENCE: 24
tgtaaaacga cggccagttt ctctcaagca ctctgcaaag cacaaac                47

<210> SEQ ID NO 25
<211> LENGTH: 52
<212> TYPE: DNA
<213> ORGANISM: Artificial Sequence
<220> FEATURE:
<223> OTHER INFORMATION: Primer

<400> SEQUENCE: 25
caggaaacag ctatgaccct accttttaat aagcctctgg gcatactgaa ta          52

<210> SEQ ID NO 26
<211> LENGTH: 47
<212> TYPE: DNA
<213> ORGANISM: Artificial Sequence
<220> FEATURE:
<223> OTHER INFORMATION: Primer

<400> SEQUENCE: 26
tgtaaaacga cggccagtag cgggattttg ttgacaattt ggggctt                47

<210> SEQ ID NO 27
<211> LENGTH: 58
<212> TYPE: DNA
<213> ORGANISM: Artificial Sequence
<220> FEATURE:
<223> OTHER INFORMATION: Primer

<400> SEQUENCE: 27
caggaaacag ctatgaccca ttggtaaaaa cttgaaaact gtaaaagaa tgcttcag     58

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
tgtaaaacga cggccagtca ccaggtagtg gaacttctgc aagag                  45

<210> SEQ ID NO 29
<211> LENGTH: 49
<212> TYPE: DNA
<213> ORGANISM: Artificial Sequence
<220> FEATURE:
<223> OTHER INFORMATION: Primer

```
<400> SEQUENCE: 29
caggaaacag ctatgaccgt ggcaattctt ggtgagagat ttctttgga          49

<210> SEQ ID NO 30
<211> LENGTH: 43
<212> TYPE: DNA
<213> ORGANISM: Artificial Sequence
<220> FEATURE:
<223> OTHER INFORMATION: Primer

<400> SEQUENCE: 30
tgtaaaacga cggccagtat gggttagcat aacaggtggg gac                43

<210> SEQ ID NO 31
<211> LENGTH: 55
<212> TYPE: DNA
<213> ORGANISM: Artificial Sequence
<220> FEATURE:
<223> OTHER INFORMATION: Primer

<400> SEQUENCE: 31
caggaaacag ctatgaccgc ttaaacataa tagaatggag cacactgtaa atgat    55

<210> SEQ ID NO 32
<211> LENGTH: 50
<212> TYPE: DNA
<213> ORGANISM: Artificial Sequence
<220> FEATURE:
<223> OTHER INFORMATION: Primer

<400> SEQUENCE: 32
tgtaaaacga cggccagtac aactacttgg atttgggtct taatgcttct          50

<210> SEQ ID NO 33
<211> LENGTH: 51
<212> TYPE: DNA
<213> ORGANISM: Artificial Sequence
<220> FEATURE:
<223> OTHER INFORMATION: Primer

<400> SEQUENCE: 33
caggaaacag ctatgaccac attcttccac ctaatcccag tttttctaag t        51

<210> SEQ ID NO 34
<211> LENGTH: 52
<212> TYPE: DNA
<213> ORGANISM: Artificial Sequence
<220> FEATURE:
<223> OTHER INFORMATION: Primer

<400> SEQUENCE: 34
tgtaaaacga cggccagtga gaaatactgt gccagaaata ctaaagaact ga       52

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
caggaaacag ctatgacctg ggcacctgta atccaagcta ctc                 43

<210> SEQ ID NO 36
<211> LENGTH: 50
```

```
<212> TYPE: DNA
<213> ORGANISM: Artificial Sequence
<220> FEATURE:
<223> OTHER INFORMATION: Primer

<400> SEQUENCE: 36
tgtaaaacga cggccagtcc agtggataat gaatgcacag aacaataaac          50

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
caggaaacag ctatgaccca tgaggaaaca gaaaggatcc cagag               45

<210> SEQ ID NO 38
<211> LENGTH: 53
<212> TYPE: DNA
<213> ORGANISM: Artificial Sequence
<220> FEATURE:
<223> OTHER INFORMATION: Primer

<400> SEQUENCE: 38
tgtaaaacga cggccagtgc aattcttagt tgactcacat tgctgaatta ctt      53

<210> SEQ ID NO 39
<211> LENGTH: 43
<212> TYPE: DNA
<213> ORGANISM: Artificial Sequence
<220> FEATURE:
<223> OTHER INFORMATION: Primer

<400> SEQUENCE: 39
caggaaacag ctatgaccga ctctcaaggg actcagtcca ctt                 43

<210> SEQ ID NO 40
<211> LENGTH: 48
<212> TYPE: DNA
<213> ORGANISM: Artificial Sequence
<220> FEATURE:
<223> OTHER INFORMATION: Primer

<400> SEQUENCE: 40
tgtaaaacga cggccagtgc ccacttttga agatgcagca ttttacag            48

<210> SEQ ID NO 41
<211> LENGTH: 55
<212> TYPE: DNA
<213> ORGANISM: Artificial Sequence
<220> FEATURE:
<223> OTHER INFORMATION: Primer

<400> SEQUENCE: 41
caggaaacag ctatgaccgt ataagaatat tgcttttacc tgctaagatt tggtc    55
```